(12) United States Patent
Ryu et al.

(10) Patent No.: US 11,766,485 B2
(45) Date of Patent: Sep. 26, 2023

(54) NANOLIPOSOME-MICROBUBBLE CONJUGATE HAVING COMPLEX OF CAS9 PROTEIN, GUIDE RNA INHIBITING SRD5A2 GENE EXPRESSION AND CATIONIC POLYMER ENCAPSULATED IN NANOLIPOSOME AND COMPOSITION FOR AMELIORATING OR TREATING HAIR LOSS CONTAINING THE SAME

(71) Applicant: MOOGENE MEDI CO., LTD., Seongnam-si (KR)

(72) Inventors: Jee-Yeon Ryu, Seoul (KR); Eun-Jeong Won, Incheon (KR); Han A Reum Lee, Seongnam-si (KR); Kyeong-Nam Yu, Seongnam-si (KR)

(73) Assignee: MOOGENE MEDI CO., LTD., Seongnam-si (KR)

( * ) Notice: Subject to any disclaimer, the term of this patent is extended or adjusted under 35 U.S.C. 154(b) by 702 days.

(21) Appl. No.: 16/646,899

(22) PCT Filed: Oct. 17, 2018

(86) PCT No.: PCT/KR2018/012251
§ 371 (c)(1),
(2) Date: Mar. 12, 2020

(87) PCT Pub. No.: WO2019/078611
PCT Pub. Date: Apr. 25, 2019

(65) Prior Publication Data
US 2021/0369859 A1    Dec. 2, 2021

(30) Foreign Application Priority Data
Oct. 18, 2017  (KR) ........................ 10-2017-0135017

(51) Int. Cl.
*A61K 47/69* (2017.01)
*C12N 9/22* (2006.01)
*C12N 15/11* (2006.01)

(52) U.S. Cl.
CPC ...... *A61K 47/6913* (2017.08); *A61K 47/6925* (2017.08); *C12N 9/22* (2013.01); *C12N 15/11* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 2010/0112040 | A1* | 5/2010 | Basheer ................ | A61P 35/00 424/450 |
| 2015/0291966 | A1* | 10/2015 | Zhang .................... | C12N 15/63 435/320.1 |
| 2015/0329857 | A1* | 11/2015 | Sassoon ................ | C12N 15/113 435/375 |

FOREIGN PATENT DOCUMENTS

| | | |
|---|---|---|
| KR | 10-2014-0018150 A | 2/2014 |
| KR | 10-1488822 B1 | 2/2015 |
| KR | 10-2016-0074883 A | 6/2016 |
| KR | 10-2016-0089526 A | 7/2016 |
| KR | 10-1683463 B1 | 12/2016 |
| KR | 10-1710026 B1 | 2/2017 |
| KR | 10-1870694 B1 | 6/2018 |
| WO | 2014/021678 A1 | 2/2014 |
| WO | WO-2014021678 A1 * | 2/2014 ........... A61K 31/337 |

OTHER PUBLICATIONS

Park et al 2016 Biol. Pharm. Bui. 39:1060-1068, provided by Applicant (Year: 2016).*
F Ann Ran, et al."Genome engineering using the CRISPR-Cas9 system", Nature Protocols, 2013, pp. 2281-2308, vol. 8, No. 11.
Je Wook Woo, et al., "DNA-free genome editing in plants with preassembled CRISPR-Cas9 ribonucleoproteins", Nature Biotechnology, 2015, pp. 1-4, vol. 33, No. 11.
Suresh Ramakrishna, et al., "Gene disruption by cell-penetrating peptide-mediated delivery of Cas9 protein and guide RNA", Genome Research, 2014, pp. 1020-1027, vol. 24, No. 6.
Venkataram Mysore, et al., "Finasteride and sexual side effects", Indian Dermatology Online Journal, Jan.-Apr. 2012, pp. 62-65, vol. 3, Issue 1.
John A. Zuris, et al., "Efficient Delivery of Genome-Editing Proteins In Vitro and In Vivo", Nat. Biotechnol., Jan. 2015, pp. 1-26, vol. 33, No. 1.
Seeun Park, et al., "Bee Venom Promotes Hair Growth in Association with Inhibiting 5a-Reductase Expression", Biol. Pharm. Bull, 2016, pp. 1060-1068, vol. 39, No. 6.
International Search Report for PCT/KR2018/012251 dated Jan. 17, 2019 (PCT/ISA/210).

* cited by examiner

*Primary Examiner* — Brent T Page
(74) *Attorney, Agent, or Firm* — Sughrue Mion, PLLC

(57) ABSTRACT

The present invention relates to a nanoliposome-microbubble conjugate, in which a complex of a Cas9 protein, a guide RNA inhibiting SRD5A2 gene expression and a cationic polymer is encapsulated in a nanoliposome, and to a composition for the amelioration or treatment of hair loss containing the same. Currently, drugs used for the treatment of hair loss cause serious side effects such as loss of libido or erectile dysfunction, and hair loss progresses again when drug treatment is stopped. However, when the nanoliposome-microbubble conjugate of the present invention is used, the expression of SRD5A2 inducing hair loss can be fundamentally suppressed, and the treatment of male hair loss can be performed very effectively.

6 Claims, 20 Drawing Sheets
Specification includes a Sequence Listing.

SEQUENCE LISTING

```
<160> NUMBER OF SEQ ID NOS: 67

<210> SEQ ID NO 1
<211> LENGTH: 20
<212> TYPE: RNA
<213> ORGANISM: Homo sapiens

<400> SEQUENCE: 1
guguacucac ugcucaaucg                                                    20

<210> SEQ ID NO 2
<211> LENGTH: 20
<212> TYPE: RNA
<213> ORGANISM: Homo sapiens

<400> SEQUENCE: 2
aggggccgaa cgcuuguaau                                                    20

<210> SEQ ID NO 3
<211> LENGTH: 20
<212> TYPE: RNA
<213> ORGANISM: Homo sapiens

<400> SEQUENCE: 3
acuauauauu gcgccagcuc                                                    20

<210> SEQ ID NO 4
<211> LENGTH: 20
<212> TYPE: RNA
<213> ORGANISM: Homo sapiens

<400> SEQUENCE: 4
cacagacaua cgguuuagcu                                                    20

<210> SEQ ID NO 5
<211> LENGTH: 20
<212> TYPE: RNA
<213> ORGANISM: Homo sapiens

<400> SEQUENCE: 5
```
uccauucaau gaucucaccg                                          20

<210> SEQ ID NO 6
<211> LENGTH: 20
<212> TYPE: DNA
<213> ORGANISM: Homo sapiens

<400> SEQUENCE: 6
gtgtactcac tgctcaatcg                                          20

<210> SEQ ID NO 7
<211> LENGTH: 20
<212> TYPE: DNA
<213> ORGANISM: Homo sapiens

<400> SEQUENCE: 7
aggggccgaa cgcttgtaat                                          20

<210> SEQ ID NO 8
<211> LENGTH: 20
<212> TYPE: DNA
<213> ORGANISM: Homo sapiens

<400> SEQUENCE: 8
actatatatt gcgccagctc                                          20

<210> SEQ ID NO 9
<211> LENGTH: 20
<212> TYPE: DNA
<213> ORGANISM: Homo sapiens

<400> SEQUENCE: 9
cacagacata cggtttagct                                          20

<210> SEQ ID NO 10
<211> LENGTH: 20
<212> TYPE: DNA
<213> ORGANISM: Homo sapiens

<400> SEQUENCE: 10
tccattcaat gatctcaccg                                          20

<210> SEQ ID NO 11
<211> LENGTH: 20
<212> TYPE: DNA
<213> ORGANISM: Homo sapiens

<400> SEQUENCE: 11
cgattgagca gtgagtacac                                          20

<210> SEQ ID NO 12
<211> LENGTH: 20
<212> TYPE: DNA
<213> ORGANISM: Homo sapiens

<400> SEQUENCE: 12
attacaagcg ttcggcccct                                          20

<210> SEQ ID NO 13
<211> LENGTH: 20
<212> TYPE: DNA
<213> ORGANISM: Homo sapiens

<400> SEQUENCE: 13

```
gagctggcgc aatatatagt                                              20

<210> SEQ ID NO 14
<211> LENGTH: 20
<212> TYPE: DNA
<213> ORGANISM: Homo sapiens

<400> SEQUENCE: 14
agctaaaccg tatgtctgtg                                              20

<210> SEQ ID NO 15
<211> LENGTH: 20
<212> TYPE: DNA
<213> ORGANISM: Homo sapiens

<400> SEQUENCE: 15
cggtgagatc attgaatgga                                              20

<210> SEQ ID NO 16
<211> LENGTH: 20
<212> TYPE: RNA
<213> ORGANISM: Mus musculus

<400> SEQUENCE: 16
acagacaugc gguuuagcgu                                              20

<210> SEQ ID NO 17
<211> LENGTH: 20
<212> TYPE: RNA
<213> ORGANISM: Mus musculus

<400> SEQUENCE: 17
cgcgcaauaa accagguaau                                              20

<210> SEQ ID NO 18
<211> LENGTH: 20
<212> TYPE: RNA
<213> ORGANISM: Mus musculus

<400> SEQUENCE: 18
uccauucaau aaucucgccc                                              20

<210> SEQ ID NO 19
<211> LENGTH: 20
<212> TYPE: RNA
<213> ORGANISM: Mus musculus

<400> SEQUENCE: 19
uccugggcga gauuauugaa                                              20

<210> SEQ ID NO 20
<211> LENGTH: 20
<212> TYPE: RNA
<213> ORGANISM: Mus musculus

<400> SEQUENCE: 20
agcccggaga ggucaucuac                                              20

<210> SEQ ID NO 21
<211> LENGTH: 20
<212> TYPE: DNA
<213> ORGANISM: Mus musculus
```

<400> SEQUENCE: 21
acagacatgc ggtttagcgt                                                    20

<210> SEQ ID NO 22
<211> LENGTH: 20
<212> TYPE: DNA
<213> ORGANISM: Mus musculus

<400> SEQUENCE: 22
cgcgcaataa accaggtaat                                                    20

<210> SEQ ID NO 23
<211> LENGTH: 20
<212> TYPE: DNA
<213> ORGANISM: Mus musculus

<400> SEQUENCE: 23
tccattcaat aatctcgccc                                                    20

<210> SEQ ID NO 24
<211> LENGTH: 20
<212> TYPE: DNA
<213> ORGANISM: Mus musculus

<400> SEQUENCE: 24
tcctgggcga gattattgaa                                                    20

<210> SEQ ID NO 25
<211> LENGTH: 20
<212> TYPE: DNA
<213> ORGANISM: Mus musculus

<400> SEQUENCE: 25
agcccggaga ggtcatctac                                                    20

<210> SEQ ID NO 26
<211> LENGTH: 20
<212> TYPE: DNA
<213> ORGANISM: Mus musculus

<400> SEQUENCE: 26
acgctaaacc gcatgtctgt                                                    20

<210> SEQ ID NO 27
<211> LENGTH: 20
<212> TYPE: DNA
<213> ORGANISM: Mus musculus

<400> SEQUENCE: 27
attacctggt ttattgcgcg                                                    20

<210> SEQ ID NO 28
<211> LENGTH: 20
<212> TYPE: DNA
<213> ORGANISM: Mus musculus

<400> SEQUENCE: 28
gggcgagatt attgaatgga                                                    20

<210> SEQ ID NO 29
<211> LENGTH: 20
<212> TYPE: DNA

```
<400> SEQUENCE: 29
ttcaataatc tcgcccagga                                                   20

<210> SEQ ID NO 30
<211> LENGTH: 20
<212> TYPE: DNA
<213> ORGANISM: Mus musculus

<400> SEQUENCE: 30
gtagatgacc tctccgggct                                                   20

<210> SEQ ID NO 31
<211> LENGTH: 104
<212> TYPE: RNA
<213> ORGANISM: Artificial Sequence
<220> FEATURE:
<223> OTHER INFORMATION: gRNA for Homo sapiens

<400> SEQUENCE: 31
guguacucac ugcucaaucg guuuuagagc uagaaauagc aaguuaaaau aaggcuaguc        60
cguuaucaac uugaaaaagu ggcaccgagu cggugcuuuu uuuu                        104

<210> SEQ ID NO 32
<211> LENGTH: 104
<212> TYPE: RNA
<213> ORGANISM: Artificial Sequence
<220> FEATURE:
<223> OTHER INFORMATION: gRNA for Homo sapiens

<400> SEQUENCE: 32
aggggccgaa cgcuuguaau guuuuagagc uagaaauagc aaguuaaaau aaggcuaguc        60
cguuaucaac uugaaaaagu ggcaccgagu cggugcuuuu uuuu                        104

<210> SEQ ID NO 33
<211> LENGTH: 104
<212> TYPE: RNA
<213> ORGANISM: Artificial Sequence
<220> FEATURE:
<223> OTHER INFORMATION: gRNA for Homo sapiens

<400> SEQUENCE: 33
acuauauauu gcgccagcuc guuuuagagc uagaaauagc aaguuaaaau aaggcuaguc        60
cguuaucaac uugaaaaagu ggcaccgagu cggugcuuuu uuuu                        104

<210> SEQ ID NO 34
<211> LENGTH: 104
<212> TYPE: RNA
<213> ORGANISM: Artificial Sequence
<220> FEATURE:
<223> OTHER INFORMATION: gRNA for Homo sapiens

<400> SEQUENCE: 34
cacagacaua cgguuuagcu guuuuagagc uagaaauagc aaguuaaaau aaggcuaguc        60
cguuaucaac uugaaaaagu ggcaccgagu cggugcuuuu uuuu                        104

<210> SEQ ID NO 35
<211> LENGTH: 104
<212> TYPE: RNA
<213> ORGANISM: Artificial Sequence
<220> FEATURE:
<223> OTHER INFORMATION: gRNA for Homo sapiens
```

<400> SEQUENCE: 35
uccauucaau gaucucaccg guuuuagagc uagaaauagc aaguuaaaau aaggcuaguc    60
cguuaucaac uugaaaaagu ggcaccgagu cggugcuuuu uuuu    104

<210> SEQ ID NO 36
<211> LENGTH: 104
<212> TYPE: RNA
<213> ORGANISM: Artificial Sequence
<220> FEATURE:
<223> OTHER INFORMATION: gRNA for Mus musculus

<400> SEQUENCE: 36
acagacaugc gguuuagcgu guuuuagagc uagaaauagc aaguuaaaau aaggcuaguc    60
cguuaucaac uugaaaaagu ggcaccgagu cggugcuuuu uuuu    104

<210> SEQ ID NO 37
<211> LENGTH: 104
<212> TYPE: RNA
<213> ORGANISM: Artificial Sequence
<220> FEATURE:
<223> OTHER INFORMATION: gRNA for Mus musculus

<400> SEQUENCE: 37
cgcgcaauaa accagguaau guuuuagagc uagaaauagc aaguuaaaau aaggcuaguc    60
cguuaucaac uugaaaaagu ggcaccgagu cggugcuuuu uuuu    104

<210> SEQ ID NO 38
<211> LENGTH: 104
<212> TYPE: RNA
<213> ORGANISM: Artificial Sequence
<220> FEATURE:
<223> OTHER INFORMATION: gRNA for Mus musculus

<400> SEQUENCE: 38
uccauucaau aaucucgccc guuuuagagc uagaaauagc aaguuaaaau aaggcuaguc    60
cguuaucaac uugaaaaagu ggcaccgagu cggugcuuuu uuuu    104

<210> SEQ ID NO 39
<211> LENGTH: 104
<212> TYPE: RNA
<213> ORGANISM: Artificial Sequence
<220> FEATURE:
<223> OTHER INFORMATION: gRNA for Mus musculus

<400> SEQUENCE: 39
uccugggcga gauuauugaa guuuuagagc uagaaauagc aaguuaaaau aaggcuaguc    60
cguuaucaac uugaaaaagu ggcaccgagu cggugcuuuu uuuu    104

<210> SEQ ID NO 40
<211> LENGTH: 104
<212> TYPE: RNA
<213> ORGANISM: Artificial Sequence
<220> FEATURE:
<223> OTHER INFORMATION: gRNA for Mus musculus

<400> SEQUENCE: 40
agcccggaga ggucaucuac guuuuagagc uagaaauagc aaguuaaaau aaggcuaguc    60
cguuaucaac uugaaaaagu ggcaccgagu cggugcuuuu uuuu    104

<210> SEQ ID NO 41
<211> LENGTH: 20

```
<212> TYPE: RNA
<213> ORGANISM: Artificial Sequence
<220> FEATURE:
<223> OTHER INFORMATION: scramble gRNA

<400> SEQUENCE: 41
gcacuaccag agcuaacuca                                              20

<210> SEQ ID NO 42
<211> LENGTH: 37
<212> TYPE: DNA
<213> ORGANISM: Homo sapiens

<400> SEQUENCE: 42
tcatagtgac tatatattgc gccagctcag ggaagcc                           37

<210> SEQ ID NO 43
<211> LENGTH: 36
<212> TYPE: DNA
<213> ORGANISM: Homo sapiens

<400> SEQUENCE: 43
tcatagtgac tatatattgc gccagctcag gaagcc                            36

<210> SEQ ID NO 44
<211> LENGTH: 20
<212> TYPE: DNA
<213> ORGANISM: Artificial Sequence
<220> FEATURE:
<223> OTHER INFORMATION: SRD5A2 sense

<400> SEQUENCE: 44
ggcctcttct gcgtagatta                                              20

<210> SEQ ID NO 45
<211> LENGTH: 20
<212> TYPE: DNA
<213> ORGANISM: Artificial Sequence
<220> FEATURE:
<223> OTHER INFORMATION: SRD5A2 antisense

<400> SEQUENCE: 45
cacccaagct aaaccgtatg                                              20

<210> SEQ ID NO 46
<211> LENGTH: 19
<212> TYPE: DNA
<213> ORGANISM: Artificial Sequence
<220> FEATURE:
<223> OTHER INFORMATION: GAPDH sense

<400> SEQUENCE: 46
gcaccgtcaa ggctgagaa                                               19

<210> SEQ ID NO 47
<211> LENGTH: 19
<212> TYPE: DNA
<213> ORGANISM: Artificial Sequence
<220> FEATURE:
<223> OTHER INFORMATION: GAPDH antisense

<400> SEQUENCE: 47
agggatctcg ctcctggaa                                               19

<210> SEQ ID NO 48
```

```
<211> LENGTH: 21
<212> TYPE: DNA
<213> ORGANISM: Artificial Sequence
<220> FEATURE:
<223> OTHER INFORMATION: A portion of the scaffold sequence

<400> SEQUENCE: 48
gttttagagc tagaaatagc a                                              21

<210> SEQ ID NO 49
<211> LENGTH: 69
<212> TYPE: DNA
<213> ORGANISM: Artificial Sequence
<220> FEATURE:
<223> OTHER INFORMATION: SRD5A2 forward primer sgRNA1

<400> SEQUENCE: 49
gcggcctcta atacgactca ctagggggt gtactcactg ctcaatcggt tttagagcta      60
gaaatagca                                                            69

<210> SEQ ID NO 50
<211> LENGTH: 69
<212> TYPE: DNA
<213> ORGANISM: Artificial Sequence
<220> FEATURE:
<223> OTHER INFORMATION: SRD5A2 forward primer sgRNA2

<400> SEQUENCE: 50
gcggcctcta atacgactca ctagggag gggccgaacg cttgtaatgt tttagagcta       60
gaaatagca                                                            69

<210> SEQ ID NO 51
<211> LENGTH: 69
<212> TYPE: DNA
<213> ORGANISM: Artificial Sequence
<220> FEATURE:
<223> OTHER INFORMATION: SRD5A2 forward primer sgRNA3

<400> SEQUENCE: 51
gcggcctcta atacgactca ctagggac tatatattgc gccagctcgt tttagagcta       60
gaaatagca                                                            69

<210> SEQ ID NO 52
<211> LENGTH: 69
<212> TYPE: DNA
<213> ORGANISM: Artificial Sequence
<220> FEATURE:
<223> OTHER INFORMATION: SRD5A2 forward primer sgRNA4

<400> SEQUENCE: 52
gcggcctcta atacgactca ctagggca cagacatacg gtttagctgt tttagagcta       60
gaaatagca                                                            69

<210> SEQ ID NO 53
<211> LENGTH: 69
<212> TYPE: DNA
<213> ORGANISM: Artificial Sequence
<220> FEATURE:
<223> OTHER INFORMATION: SRD5A2 forward primer sgRNA5

<400> SEQUENCE: 53
gcggcctcta atacgactca ctagggtc cattcaatga tctcaccggt tttagagcta       60
gaaatagca                                                            69
```

<210> SEQ ID NO 54
<211> LENGTH: 69
<212> TYPE: DNA
<213> ORGANISM: Artificial Sequence
<220> FEATURE:
<223> OTHER INFORMATION: Mouse SRD5A2 forward primer sgRNAm1

<400> SEQUENCE: 54
gcggcctcta atacgactca ctatagggac agacatgcgg tttagcgtgt tttagagcta     60
gaaatagca                                                            69

<210> SEQ ID NO 55
<211> LENGTH: 69
<212> TYPE: DNA
<213> ORGANISM: Artificial Sequence
<220> FEATURE:
<223> OTHER INFORMATION: Mouse SRD5A2 forward primer sgRNAm2

<400> SEQUENCE: 55
gcggcctcta atacgactca ctatagggcg cgcaataaac caggtaatgt tttagagcta     60
gaaatagca                                                            69

<210> SEQ ID NO 56
<211> LENGTH: 69
<212> TYPE: DNA
<213> ORGANISM: Artificial Sequence
<220> FEATURE:
<223> OTHER INFORMATION: Mouse SRD5A2 forward primer sgRNAm3

<400> SEQUENCE: 56
gcggcctcta atacgactca ctatagggcg cgcaataaac caggtaatgt tttagagcta     60
gaaatagca                                                            69

<210> SEQ ID NO 57
<211> LENGTH: 69
<212> TYPE: DNA
<213> ORGANISM: Artificial Sequence
<220> FEATURE:
<223> OTHER INFORMATION: Mouse SRD5A2 forward primer sgRNAm4

<400> SEQUENCE: 57
gcggcctcta atacgactca ctatagggtc ctgggcgaga ttattgaagt tttagagcta     60
gaaatagca                                                            69

<210> SEQ ID NO 58
<211> LENGTH: 69
<212> TYPE: DNA
<213> ORGANISM: Artificial Sequence
<220> FEATURE:
<223> OTHER INFORMATION: Mouse SRD5A2 forward primer sgRNAm5

<400> SEQUENCE: 58
gcggcctcta atacgactca ctatagggag cccggagagg tcatctacgt tttagagcta     60
gaaatagca                                                            69

<210> SEQ ID NO 59
<211> LENGTH: 21
<212> TYPE: DNA
<213> ORGANISM: Artificial Sequence
<220> FEATURE:
<223> OTHER INFORMATION: Reverse primer

<400> SEQUENCE: 59
aaaagcaccg actcggtgcc a                                              21

<210> SEQ ID NO 60
<211> LENGTH: 20
<212> TYPE: DNA
<213> ORGANISM: Artificial Sequence
<220> FEATURE:
<223> OTHER INFORMATION: Forward primer

<400> SEQUENCE: 60
ttgccctccc cactttctgc                                                20

<210> SEQ ID NO 61
<211> LENGTH: 20
<212> TYPE: DNA
<213> ORGANISM: Artificial Sequence
<220> FEATURE:
<223> OTHER INFORMATION: Reverse primer

<400> SEQUENCE: 61
tcccaccttc cgggtattgc                                                20

<210> SEQ ID NO 62
<211> LENGTH: 23
<212> TYPE: DNA
<213> ORGANISM: Artificial Sequence
<220> FEATURE:
<223> OTHER INFORMATION: Forward primer

<400> SEQUENCE: 62
ctctttggac tattttgtgg ctt                                            23

<210> SEQ ID NO 63
<211> LENGTH: 23
<212> TYPE: DNA
<213> ORGANISM: Artificial Sequence
<220> FEATURE:
<223> OTHER INFORMATION: Reverse primer

<400> SEQUENCE: 63
aagactggga acatttggtt tgt                                            23

<210> SEQ ID NO 64
<211> LENGTH: 23
<212> TYPE: DNA
<213> ORGANISM: Artificial Sequence
<220> FEATURE:
<223> OTHER INFORMATION: Foward primer

<400> SEQUENCE: 64
ggcaggaagc ccctcaggga gat                                            23

<210> SEQ ID NO 65
<211> LENGTH: 23
<212> TYPE: DNA
<213> ORGANISM: Artificial Sequence
<220> FEATURE:
<223> OTHER INFORMATION: Reverse primer

<400> SEQUENCE: 65
aatgtgaccg gctgcttcaa gtt                                            23

<210> SEQ ID NO 66
<211> LENGTH: 23

```
<212> TYPE: DNA
<213> ORGANISM: Artificial Sequence
<220> FEATURE:
<223> OTHER INFORMATION: Forward primer

<400> SEQUENCE: 66
aacccaaaac caaacacaaa acc                                          23

<210> SEQ ID NO 67
<211> LENGTH: 23
<212> TYPE: DNA
<213> ORGANISM: Artificial Sequence
<220> FEATURE:
<223> OTHER INFORMATION: Reverse primer

<400> SEQUENCE: 67
gggtcataga catgtgcacc atg                                          23
```

NANOLIPOSOME-MICROBUBBLE CONJUGATE HAVING COMPLEX OF CAS9 PROTEIN, GUIDE RNA INHIBITING SRD5A2 GENE EXPRESSION AND CATIONIC POLYMER ENCAPSULATED IN NANOLIPOSOME AND COMPOSITION FOR AMELIORATING OR TREATING HAIR LOSS CONTAINING THE SAME

CROSS REFERENCE TO RELATED APPLICATIONS

This application is a National Stage of International Application No. PCT/KR2018/012251 filed Oct. 17, 2018, claiming priority based on Korean Patent Application No. 10-2017-0135017 filed Oct. 18, 2017, the entire contents of which are incorporated herein by reference.

TECHNICAL FIELD

The present invention relates to a nanoliposome-microbubble conjugate, in which a complex of a Cas9 protein, a guide RNA inhibiting SRD5A2 gene expression and a cationic polymer is encapsulated in a nanoliposome, and to a composition for ameliorating or treating hair loss containing the same.

More particularly, the present invention relates to a nanoliposome-microbubble conjugate, configured such that a nanoliposome having encapsulated therein a complex of a Cas9 protein, a guide RNA inhibiting SRD5A2 gene expression and a cationic polymer is chemically stably conjugated to a microbubble having a hydrophobic gas therein, and to a composition for the amelioration or treatment of hair loss containing the same.

BACKGROUND ART

Gene-editing technology, derived from the adaptive immunity of microorganisms, began focused on an immune system in which bacteriophage fragments are remembered as DNA by bacteriophage infection and then the corresponding DNA is cleaved with Cas9 (CRISPR-associated protein 9: RNA-guided DNA endonuclease enzyme), which is a nuclease acting as gene scissors, upon secondary infection. This has developed into genetic correction technology that allows the corresponding site to be cleaved with a Cas9 protein if the specific base sequence is recognized by a guide RNA (gRNA) (Ran F A et al., 2013, Woo J W et al., 2015).

This technology is receiving attention as a method of treating the fundamental cause of gene-mutation-induced diseases, which are regarded as incurable diseases. However, there remain problems to be solved, such as efficient in-vivo delivery of the gene-editing system and off-targeting of genes other than the target gene. In particular, the safety of the gene-editing system using a Cas9 plasmid, which was initially used, needs to be verified with regard to various immune responses and antibiotic resistance upon in-vivo delivery. Recently, a system for producing gene scissors (Cas9) composed of protein and guide RNA in vitro and delivering them has been applied as an alternative thereto, but also has problems related to efficient delivery into cells and the stability of protein and RNA (Ramakrishna S et al., 2014).

Hair loss generally refers to the loss of thick black hair from the scalp. The causes of hair loss are various, but genetics and the male hormone androgen are considered to be important factors. Of these, male androgenic alopecia, which accounts for about 60 to 70% of hair loss, progresses in a manner in which testosterone is converted into dihydrotestosterone (DHT) by 5-alpha reductase (SRD5A) and excessively produced dihydrotestosterone binds to the androgenic receptor (AR) of dermal papilla cells (DPCs) to thus induce apoptosis, leading to hair loss due to miniaturization of the hair. Since males with a lot of expression of the 5-alpha reductase, particularly 5-alpha reductase type 2 (SRD5A2), which is mainly distributed in the dermal papillae and outer root sheath of hair follicles, or persons having high activity of 5-alpha reductase type 2 have a quite large amount of dihydrotestosterone compared to most men, the possibility of hair loss is increased. Hence, the main treatment for male androgenic alopecia is to lower the amount or activity of 5-alpha reductase type 2 in order to prevent the conversion of testosterone into dihydrotestosterone.

Drugs currently developed as therapeutic agents for hair loss include Propecia, Minoxidil, and Dutasteride. Propecia functions to directly inhibit 5-alpha reductase type 2, and Dutasteride functions to inhibit 5-alpha reductase type 1 and type 2 to thus prevent the conversion of testosterone into dihydrotestosterone, thereby reducing the progression of hair loss. However, side effects such as loss of libido, erectile dysfunction, etc. occur in patients who take it, and hair loss resumes when administration of the drug is discontinued. In particular, the USFDA recommends that men with infertility or low sperm counts stop taking the drug, and fertile women are prohibited from taking the drug because such a drug may cause male sexual dysfunction in the fetus (Myscore V et al., 2012).

SRD5A2 is one of the genes associated with hair loss, and thus it is considered important to reduce SRD5A2 gene expression because it is associated with dihydrotestosterone, which induces apoptosis.

Meanwhile, two important properties required in intracellular drug delivery systems are efficiency and cytotoxicity (safety), and nanoliposome carrier technology composed of cholesterol or lipid is widely used (Zuris J A et al., 2015). However, this nanoliposome technology alone does not facilitate drug delivery into the dermis, which is present below the stratum corneum, which acts as a skin barrier (Nemes Z et al., 1999).

A microbubble, which is an FDA-approved diagnostic ultrasound contrast agent, is provided in the form of a micro-sized bubble filled with a hydrophobic gas. A microbubble technique causes cavitation when the microbubble is exposed to ultrasound to thus temporarily form pores in the cell membrane of the surrounding cells, whereby the nanoliposome may be effectively delivered into the cells using sonoporation, through which a material penetrates cells through the pores thus formed, unlike other cell delivery methods.

Therefore, the present inventors applied the microbubble technique to the nanoliposome in order to efficiently deliver the nanoliposome, which inhibits the SRD5A2 gene expression, to the dermal layer, and preferably, have prepared a composition in which a nanoliposome having encapsulated therein a complex of a Cas9 protein, a guide RNA inhibiting SRD5A2 gene expression and a cationic polymer is conjugated to a microbubble. Thereby, a carrier having good drug delivery efficiency into the dermis is prepared and used as a composition for the amelioration or treatment of hair loss, thus culminating in the present invention.

CITATION LIST

Patent Literature (Patent Document 1) Korean Patent No. 10-1710026 (Invention Title: Nanoliposome carrier composition containing hybrid of Cas9 protein and guide RNA, Applicant: Moogene Medi, Registration Date: Feb. 20, 2017)
(Patent Document 2) Korean Patent No. 10-1683463 (Invention Title: Microbubble-Liposome-Melanin nanoparticle complex and Contrast agent comprising the same, Applicant: Seoul National University Industry-Academic Cooperation Foundation, Registration Date: Dec. 1, 2016)

(Patent Document 3) Korean Patent Application Publication No. 10-2016-0089526 (Invention Title: Delivery, use and therapeutic applications of the CRISPR-CAS systems and compositions for targeting disorders and diseases using particle delivery components, Applicant: Seoul National University Industry-Academic Cooperation Foundation, Laid-open Date: Jul. 27, 2016)

Non-Patent Literature (Non-Patent Document 1) Ran R A et al., Genome engineering using the CRISPR-Cas9 system, Nat. Protoc., 2013, 8(11), 2281-2308.

(Non-Patent Document 2) Woo J W et al., DNA-free genome editing in plants with preassembled CRISPR-Cas9 ribonucleoproteins, Nat. Biotechnol., 2015, 33(11), 1162-1164.

(Non-Patent Document 3) Ramakrishna S et al., Gene disruption by cell-penetrating peptide-mediated delivery of Cas9 protein and guide RNA, Genome Res, 2014, 24(6), 1020-1027.

(Non-Patent Document 4) Mysore V et al., Finasteride and sexual side effects, Indian Dermatol Online J, 2012, 3(1), 62-65.

(Non-Patent Document 5) Zuris J A et al., Cationic lipid-mediated delivery of proteins enables efficient protein-based genome editing in vitro and in vivo, Nat. Biotechnol., 2015, 33(1), 73-80.

DISCLOSURE

Technical Problem

Accordingly, the present invention is intended to provide a nanoliposome-microbubble conjugate, in which a complex of a Cas9 protein, a guide RNA inhibiting SRD5A2 gene expression and a cationic polymer is encapsulated in a nanoliposome, and a composition for the amelioration or treatment of hair loss containing the same.

More particularly, the present invention is intended to provide a nanoliposome-microbubble conjugate, in which a nanoliposome having encapsulated therein a complex of a Cas9 protein, a guide RNA inhibiting SRD5A2 gene expression and a cationic polymer is chemically stably conjugated to a microbubble having a hydrophobic gas therein, and a composition for the amelioration or treatment of hair loss, which contains the same, thereby inhibiting the SRD5A2 gene expression.

Technical Solution

The present invention pertains to a nanoliposome-microbubble conjugate, in which a complex of a Cas9 protein, a guide RNA inhibiting SRD5A2 gene expression and a cationic polymer is encapsulated in a nanoliposome.

The guide RNA inhibiting SRD5A2 gene expression may comprise the base sequence of SEQ. ID. NO: 1, 2, 3, 4 or 5.

The nanoliposome may include lecithin, cholesterol, a cationic phospholipid and a metal chelating lipid.

The nanoliposome may bind to a monoclonal or polyclonal antibody that is able to recognize at least one protein selected from the group consisting of endoglin, CD34, keratin 18 and IL-6 (interleukin 6), which are expressed in dermal papilla cells.

The microbubble may include an amphoteric phospholipid, an anionic phospholipid, cholesterol, a cationic phospholipid and a disulfide-group-containing lipid.

The nanoliposome-microbubble conjugate may have a particle size of 800 to 1500 nm.

The present invention may provide a composition for the amelioration or treatment of hair loss containing the nanoliposome-microbubble conjugate.

In addition, the present invention provides a method of preparing a nanoliposome-microbubble conjugate that is able to selectively recognize dermal papilla cells. More preferably, the nanoliposome-microbubble conjugate is prepared by separately preparing a nanoliposome and a microbubble and then mixing them.

The nanoliposome may be prepared as follows.

Preferably, the nanoliposome is prepared by:

S1) preparing a complex of a Cas9 protein, a guide RNA inhibiting SRD5A2 gene expression and a cationic polymer, and preparing a lipid film composition by mixing lecithin, cholesterol, a cationic phospholipid and a metal chelating lipid in chloroform;

S2) adding the lipid film composition with the complex of the Cas9 protein, the guide RNA inhibiting SRD5A2 gene expression and the cationic polymer and performing sonication;

S3) subjecting the sonicated lipid film composition to freezing-thawing and then sonication;

S4) centrifuging the lipid film composition sonicated in S3 and recovering a nanoliposome that is precipitated; and S5) allowing an antibody to bind to the precipitated nanoliposome obtained in S4 using a crosslinking agent.

Also, the microbubble may be prepared as follows.

The microbubble is prepared by:

A) preparing a lipid film composition by mixing an amphoteric phospholipid, cholesterol, an anionic lipid, an amine-group-containing lipid and a disulfide-group-containing lipid in chloroform;

B) adding a glucose solution to step A and performing sonication;

C) subjecting the lipid film composition sonicated in step B to freezing-thawing and then sonication; and D) preparing a microbubble by introducing a hydrophobic gas to the lipid film composition sonicated in step C.

A nanoliposome-microbubble conjugate may be formed by mixing the microbubble thus prepared with the nanoliposome.

Hereinafter, a detailed description will be given of the present invention.

The present invention is directed to a nanoliposome-microbubble conjugate, in which a complex of a Cas9 protein, a guide RNA inhibiting SRD5A2 gene expression and a cationic polymer is encapsulated in a nanoliposome.

The Cas9 protein may be obtained from cells or strains in which a pET28a/Cas9-Cys plasmid (Cas9-Cys inserted into a pET28a(+) vector) is transformed. Preferably, the Cas9 protein is obtained by transforming a pET28a/Cas9-Cys plasmid into *Escherichia coli* and overexpressing a Cas9 protein.

Used in the present invention, the guide RNA is selected from among base sequences of SEQ. ID. NOS: 1 to 5 below, and the nanoliposome carrier composition including the guide RNA functions to ameliorate or treat hair loss by inhibiting the expression of the SRD5A2 gene.

The guide RNA of SEQ. ID. NO: 1 is derived from a portion of the DNA sequence of human (*Homo sapiens*) SRD5A2 of SEQ. ID. NO: 6 below, and targets a portion of the DNA sequence of SRD5A2 of SEQ. ID. NO: 11 below (SEQ. ID. NO: 6 and SEQ. ID. NO: 11 have base sequences complementary to each other), and SEQ. ID. NOS: 2~5 also correspond, respectively, to SEQ. ID. NOS: 7~10 and SEQ. ID. NOS: 12~15, as described above.

TABLE 1

| Guide DNA sequence | DNA sequence for transcription (preparation) of guide RNA | Target DNA sequence of guide RNA |
|---|---|---|
| SEQ. ID. NO: 1: GUGUACUCA CUGCUCAAU CG | SEQ. ID. NO: 6: GTGTACTCACTGCTCAAT CG | SEQ. ID. NO: 11: CGATTGAGCAGTGAGTA CAC |
| SEQ. ID. NO: 2: AGGGGCCGA ACGCUUGUA AU | SEQ. ID. NO: 7: AGGGGCCGAACGCTTGT AAT | SEQ. ID. NO: 12: ATTACAAGCGTTCGGCC CCT |
| SEQ. ID. NO: 3: ACUAUAUAU UGCGCCAGC UC | SEQ. ID. NO: 8: ACTATATATTGCGCCAGC TC | SEQ. ID. NO: 13: GAGCTGGCGCAATATAT AGT |
| SEQ. ID. NO: 4: CACAGACAU ACGGUUUAG CU | SEQ. ID. NO: 9: CACAGACATACGGTTTA GCT | SEQ. ID. NO: 14: AGCTAAACCGTATGTCT GTG |
| SEQ. ID. NO: 5: UCCAUUCAA UGAUCUCAC CG | SEQ. ID. NO: 10: TCCATTCAATGATCTCAC CG | SEQ. ID. NO: 15: CGGTGAGATCATTGAAT GGA |

The present invention, on the other hand, provides a nanoliposome-microbubble conjugate for animal experiments that will replace a human, which is difficult to clinically apply during research and development, and the nanoliposome-microbubble conjugate for animal experiments includes the guide RNA selected from among SEQ. ID. NOS: 16 to 20 below. The animal preferably includes a mouse (*Mus musculus*). The correspondence of individual sequences is shown in Table 2 below in the same manner as in Table 1.

TABLE 2

| Guide DNA sequence | DNA sequence for transcription (preparation) of guide RNA | Target DNA sequence of guide RNA |
|---|---|---|
| SEQ. ID. NO: 16: ACAGACAUG CGGUUUAGC GU | SEQ. ID. NO: 21: ACAGACATGCGGTTTA GCGT | SEQ. ID. NO: 26: ACGCTAAACCGCATGTCT GT |
| SEQ. ID. NO: 17: CGCGCAAUA AACCAGGUA AU | SEQ. ID. NO: 22: CGCGCAATAAACCAG GTAAT | SEQ. ID. NO: 27: ATTACCTGGTTTATTGCG CG |
| SEQ. ID. NO: 18: UCCAUUCAA UAAUCUCGC CC | SEQ. ID. NO: 23: TCCATTCAATAATCTC GCCC | SEQ. ID. NO: 28: GGGCGAGATTATTGAATG GA |
| SEQ. ID. NO: 19: UCCUGGGCG AGAUUAUUG AA | SEQ. ID. NO: 24: TCCTGGGCGAGATTAT TGAA | SEQ. ID. NO: 29: TTCAATAATCTCGCCCAG GA |
| SEQ. ID. NO: 20: AGCCCGGAG AGGUCAUCU AC | SEQ. ID. NO: 25: AGCCCGGAGAGGTCA TCTAC | SEQ. ID. NO: 30: GTAGATGACCTCTCCGGG CT |

A scaffold sequence may be included after the guide RNA sequence selected from among SEQ. ID. NOS: 1 to 5, or SEQ. ID. NOS: 16 to 20 in order to form a complex with the Cas9 protein. Here, the kind of scaffold sequence is not particularly limited, and any sequence may be used so long as it is a typical base sequence used for the preparation of the guide RNA.

Accordingly, the guide RNA, which is applied to the nanoliposome of the present invention, may include guide RNA bound to the following scaffold sequence and may thus be used for the preparation of the nanoliposome.

TABLE 3

| Guide RNA to be applied | Guide RNA bound to scaffold sequence |
|---|---|
| SEQ. ID. NO: 1: GUGUACUCACU GCUCAAUCG | SEQ. ID. NO: 31: GUGUACUCACUGCUCAAUCGGUUUUAGAGCUAGAAAUAGCAAGUUAAAAUAAGGCUAGUCCGUUAUCAACUUGAAAAAGUGGCACCGAGUCGGUGCUUUUUUUU |
| SEQ. ID. NO: 2: AGGGGCCGAAC GCUUGUAAU | SEQ. ID. NO: 32: AGGGGCCGAACGCUUGUAAUGUUUUAGAGCUAGAAAUAGCAAGUUAAAAUAAGGCUAGUCCGUUAUCAACUUGAAAAAGUGGCACCGAGUCGGUGCUUUUUUUU |
| SEQ. ID. NO: 3: ACUAUAUAUUG CGCCAGCUC | SEQ. ID. NO: 33: ACUAUAUAUUGCGCCAGCUCGUUUUAGAGCUAGAAAUAGCAAGUUAAAAUAAGGCUAGUCCGUUAUCAACUUGAAAAAGUGGCACCGAGUCGGUGCUUUUUUUU |
| SEQ. ID. NO: 4: CACAGACAUAC GGUUUAGCU | SEQ. ID. NO: 34: CACAGACAUACGGUUUAGCUGUUUUAGAGCUAGAAAUAGCAAGUUAAAAUAAGGCUAGUCCGULTAUCAACUUGAAAAAGUGGCACCGAGUCGGUGCUUUUUUUU |
| SEQ. ID. NO: 5: UCCAUUCAAUG AUCUCACCG | SEQ. ID. NO: 35: UCCAUUCAAUGAUCUCACCGGUUUUAGAGCUAGAAAUAGCAAGUUAAAAUAAGGCUAGUCCGUUAUCAACUUGAAAAAGUGGCACCGAGUCGGUGCUUUUUUUU |
| SEQ. ID. NO: 16: ACAGACAUGCGG UUUAGCGU | SEQ. ID. NO: 36: ACAGACAUGCGGUUUAGCGUGUUUUAGAGCUAGAAAUAGCAAGUUAAAAUAAGGCUAGUCCGUUAUCAACUUGAAAAAGUGGCACCGAGUCGGUGCUUUUUUUU |
| SEQ. ID. NO: 17: CGCGCAAUAAAC CAGGUAAU | SEQ. ID. NO: 37: CGCGCAAUAAACCAGGUAAUGUUUUAGAGCUAGAAAAUAGCAAGUUAAAAUAAGGCUAGUCCGUUAUCAACUUGAAAAAGUGGCACCGAGUCGGUGCUUUUUUUU |
| SEQ. ID. NO: 18: UCCAUUCAAUAA UCUCGCCC | SEQ. ID. NO: 38: UCCAUUCAAUAAUCUCGCCCGUUUUAGAGCUAGAAAUAGCAAGUUAAAAUAAGGCUAGUCCGUUAUCAACUUGAAAAAGUGGCACCGAGUCGGUGCUUUUUUUU |
| SEQ. ID. NO: 19: UCCUGGGCGAGA UUAUUGAA | SEQ. ID. NO: 39: UCCUGGGCGAGAUUAUUGAAGUUUUAGAGCUAGAAAUAGCAAGUUAAAAUAAGGCUAGUCCGUUAUCAACUUGAAAAAGUGGCACCGAGUCGGUGCUUUUUUUU |

TABLE 3-continued

| Guide RNA to be applied | Guide RNA bound to scaffold sequence |
|---|---|
| SEQ. ID. NO: 20: AGCCCGGAGAGGUCAUCUAC | SEQ. ID. NO: 40: AGCCCGGAGAGGUCAUCUACGUUUUAGAGCUAGAAAUAGCAAGUUAAAAUAAGGCUAGUCCGUUAUCAACUUGAAAAAGUGGCACCGAGUCGGUGCUUUUUUU |

The DNA sequences of SEQ. ID. NOS: 11 to 15 targeted by the base sequences of the guide RNA of SEQ. ID. NOS: 1 to 5 are base sequences present in SRD5A2 (*Homo sapiens* Chromosome 17, GenBank No. NC_000002.12), and the above DNA is cleaved with the guide RNA of SEQ. ID. NOS: 1 to 5.

The DNA sequences of SEQ. ID. NOS: 26 to 30 targeted by the base sequences of the guide RNA of SEQ. ID. NOS: 16 to 20 are base sequences present in SRD5A2 (*Mus musculus*, Chromosome 17, GenBank No. NC_000083.6), and the above DNA is cleaved with the guide RNA of SEQ. ID. NOS: 16 to 20.

The guide RNA of SEQ. ID. NOS: 31 to 40 may be synthesized through in-vitro transcription using T7 RNA polymerase.

The cationic polymer preferably includes at least one selected from among poly-L-lysine, polyamidoamine, poly[2-(N,N-dimethylamino)ethyl methacrylate], chitosan, poly-L-ornithine, cyclodextrin, histone, collagen, dextran and polyethyleneimine. Most preferably, polyethyleneimine is used.

The nanoliposome may include lecithin (α-phosphatidylcholine), a cationic phospholipid, cholesterol and a metal chelating lipid, thereby forming a membrane that constitutes a nanoliposome by the lecithin, cationic phospholipid, cholesterol and metal chelating lipid.

Lecithin is widely distributed in animals/plants and has excellent biocompatibility and the stability thereof has been previously verified, and thus lecithin is broadly useful in food and medicine carrier techniques.

Furthermore, it may be used as a material that facilitates control of the size and change of the shape of the nanoliposome.

The cationic phospholipid may include at least one selected from the group consisting of dioleoyl phosphatidylethanolamine (DOPE), 1,2-diphytanoyl-sn-glycero-3-phosphoethanolamine (DPhPE), 1,2-distearoyl-sn-glycero-3-phosphoethanolamine (DSPE), 1,2-dipalmitoyl-sn-glycero-3-phosphoethanolamine (DPPE) and 1,2-dioleoyl-sn-glycero-3-phosphocholine (DOPC). Preferably useful is 1,2-dipalmitoyl-sn-glycero-3-phosphoethanolamine (DPPE).

The metal chelating lipid preferably includes at least one selected from the group consisting of DOGS-NTA-Ni lipid, DMPE-DTPA-Gd lipid, and DMPE-DTPA-Cu lipid. The DOGS-NTA-Ni lipid is a lipid having the chemical structure represented by Chemical Formula 1 below:

[Chemial Formula 1]

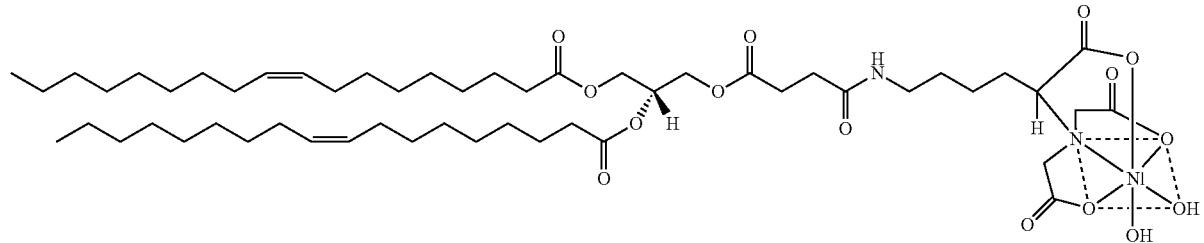

and is referred to as 1,2-dioleoyl-sn-glycero-3-[(N-(5-amino-1-carboxypentyl)iminodiacetic acid)succinyl] (nickel salt).

1,2-dioleoyl-sn-glycero-3-[(N-(5-amino-1-carboxypentyl)iminodiacetic acid)succinyl] (Nickel Salt)

The DMPE-DTPA-Gd lipid is a lipid having the chemical structure represented by Chemical Formula 2 below:

[Chemical Formula 2]

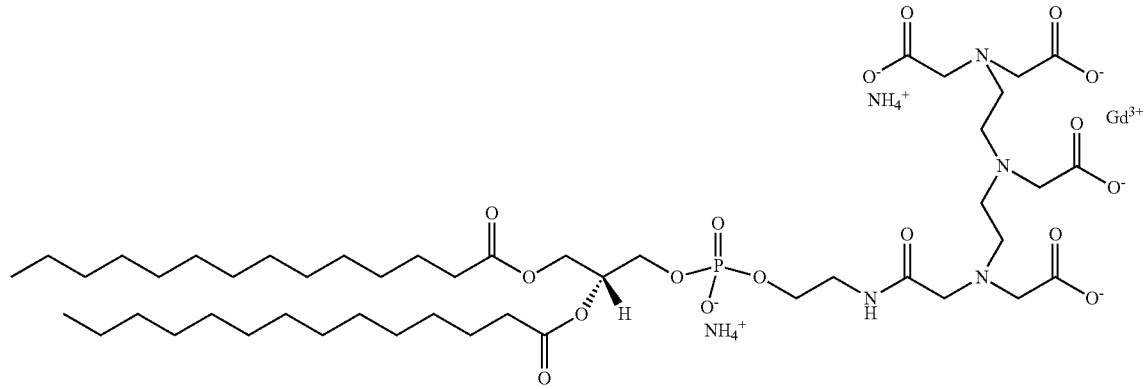

and is referred to as 1,2-dimyristoyl-sn-glycero-3-phosphoethanolamine-N-diethylenetriaminepentaacetic acid (gadolinium salt).

1,2-dimyristoyl-sn-glycero-3-phosphoethanolamine-N-diethylenetriaminepentaacetic acid (Gadolinium Salt)

The DMPE-DTPA-Cu lipid is a lipid having the chemical structure represented by Chemical Formula 3 below:

[Chemical Formula 3]

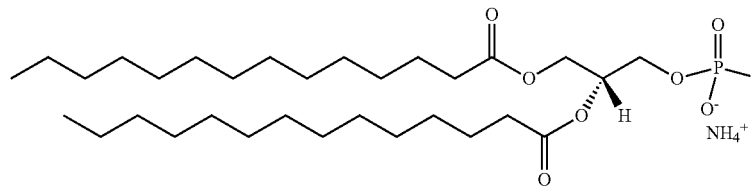
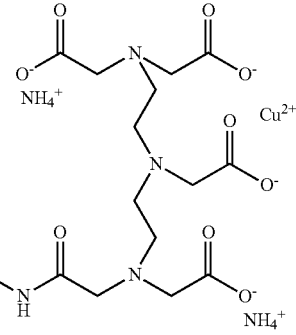

and is referred to as 1,2-dimyristoyl-sn-glycero-3-phosphoethanolamine-N-diethylenetriaminepentaacetic acid (copper salt).

1,2-dimyristoyl-sn-glycero-3-phosphoethanolamine-N-diethylenetriaminepentaacetic acid (Copper Salt)

The DOGS-NTA-Ni lipid functions to effectively encapsulate the Cas9 protein (including His-Tag) into the nanoliposome using $Ni^{2+}$ affinity and His-Tag (6×histidine) used in the protein purification process. More specifically, the DOGS-NTA-Ni is configured such that one double bond is formed on 18 carbon atoms and is thus able to form a lipid with lecithin, and $Ni^{2+}$ is attached to the end thereof, and thus two (His-Tag)s attached to the Cas9 protein and one $Ni^{2+}$ are linked with each other, whereby the Cas9 protein is more efficiently encapsulated into the nanoliposome. The DMPE-DTPA-Gd lipid and the DMPE-DTPA-Cu lipid play the same role as above, and effectively induce the encapsulation of the complex including the Cas9 protein into the nanoliposome.

The nanoliposome of the present invention may include the Cas9 protein bound to the single kind of guide RNA, or a combination of the Cas9 protein bound to each guide RNA (e.g.: 'Cas9 protein-guide RNA of SEQ. ID. NO: 1', 'Cas9 protein-guide RNA of SEQ. ID. NO: 2', etc.).

The nanoliposome is capable of binding to a monoclonal or polyclonal antibody that is able to recognize a protein selected from the group consisting of endoglin, CD34, keratin 18 and IL-6, which are expressed in dermal papilla cells.

The antibody may be easily produced using techniques widely known in the art. The polyclonal antibody may be obtained from the serum collected after injection of an antigen protein selected from the group consisting of endoglin, CD34, keratin 18 and IL-6 into an animal. The animal may include any animal host such as goat, rabbit, pig, etc.

The monoclonal antibody may be prepared using a hybridoma process (Kohler G. and Milstein C.), or a phage antibody library process (Clackson et al.; Marks et al.), as widely known in the art to which the present invention belongs. The hybridoma process may be conducted using cells of an immunologically relevant host animal, such as a mouse, and a cancer or myeloma cell line. Then, through a process using polyethylene glycol, as widely known in the art to which the present invention belongs, the two kinds of cells are fused, after which the antibody-producing cells may be proliferated through a standard tissue culture process. Then, a uniform cell population is obtained through subcloning using a limited dilution technique, after which hybridoma capable of producing an antibody specific to the above antigen protein may be mass-cultured in vitro or in vivo using a standard technique.

The phage antibody library process may be performed in a manner in which an antibody gene to the antigen protein selected from the group consisting of endoglin, CD34, keratin 18 and IL-6 is obtained and expressed in the form of a fusion protein on the surface of a phage to thus manufacture an antibody library in vitro, after which a monoclonal antibody that binds to the above antigen protein is separated from the library and thus produced. The antibody thus produced may be separated through electrophoresis, dialysis, ion exchange chromatography, affinity chromatography, and the like.

The antibody may comprise a functional fragment of an antibody molecule as well as a complete form having two full-length light chains and two full-length heavy chains. A functional fragment of an antibody molecule is a fragment having at least an antigen-binding function, and includes Fab, F(ab'), F(ab')2, F(ab)2, Fv and the like.

In the present invention, the antibody may bind using, as a linker, at least one crosslinking agent selected from the group consisting of 1,4-bis-maleimidobutane, 1,11-glycol, bis-maleimidotetraethylene 1-ethyl-3-[3-dimethylaminopropyl]carbodiimide hydrochloride, succinimidyl-4-[N-maleimidomethylcyclohexane-1-carboxy-[6-amidocaproate]] and sulfonates thereof (sulfo-SMCC), succinimidyl 6-[3-(2-pyridyldithio)-propionamide]hexanoate and sulfonates thereof (sulfo-SPDP), m-maleimidobenzoyl-N-hydroxysuccinimide ester and sulfonates thereof (sulfo-MBS), and succinimidyl [4-(p-maleimidophenyl)butylate] and sulfonates thereof (sulfo-SMPB).

The linker functions to link the cationic phospholipid of the nanoliposome and the antibody to each other.

The nanoliposome of the present invention may be stably dispersed in neutral water, cell broth, blood or the like for several hours or more.

The microbubble of the present invention may include an amphoteric phospholipid, an anionic phospholipid, cholesterol, a cationic phospholipid and a disulfide-group-containing lipid, and is prepared by forming a membrane that constitutes the bubble through the hydrophobic gas introduced to the lipid film composition comprising the mixture thereof.

The amphoteric phospholipid may be selected from the group consisting of 1,2-dipalmitoyl-sn-glycero-3-phosphocholine (DPPC), 1,2-distearoyl-sn-glycero-3-phosphocholine (DSPC), 1,2-dimyristoyl-sn-glycero-3-phosphocholine (DMPC), 1,2-dioleoyl-sn-glycero-3-phosphocholine (DOPC), 1-myristoyl-2-palmitoyl-sn-glycero-3-phosphocholine (MPPC) and 1-myristoyl-2-stearoyl-sn-glycero-3-phosphocholine (MSPC). Preferably, 1,2-dipalmitoyl-sn-glycero-3-phosphocholine (DPPC) is used.

The anionic phospholipid may include at least one selected from the group consisting of dicetyl phosphate (DCP), 1,2-dierucoyl-sn-glycero-3-phosphate (DEPA), 1,2-dilauroyl-sn-glycero-3-phosphate (DLPA), 1,2-dimyristoyl-sn-glycero-3-phosphate (DMPA) and 1,2-dioleoyl-sn-glycero-3-phosphate (DOPA). Preferably, dicetyl phosphate (DCP) is used.

As the cationic phospholipid, the same cationic phospholipid used for the preparation of the nanoliposome may be used, and more specifically, the cationic phospholipid may include at least one selected from the group consisting of dioleoyl phosphatidylethanolamine (DOPE), 1,2-diphytanoyl-sn-glycero-3-phosphoethanolamine (DPhPE), 1,2-distearoyl-sn-glycero-3-phosphoethanolamine (DSPE), 1,2-dipalmitoyl-sn-glycero-3-phosphoethanolamine (DPPE) and 1,2-dioleoyl-sn-glycero-3-phosphocholine (DOPC). Preferably, 1,2-dipalmitoyl-sn-glycero-3-phosphoethanolamine (DPPE) is used.

The disulfide-group-containing lipid may be exemplified by 1,2-distearoyl-sn-glycero-3-phosphoethanolamine-N-poly(ethylene glycol)-2000-N-[3-(2-pyridyldithio)propionate, called DSPE-PEG-sPDP.

DSPE-PEG-sPDP: 1,2-distearoyl-sn-glycero-3-phosphoethanolamine-N-poly(ethyleneglycol)-2000-N-[3-(2-pyridyldithio) propionate The DSPE-PEG-sPDP lipid is a lipid having the chemical structure of Chemical Formula 4 below.

erably, DPPC:DCP:cholesterol:DPPE:sPDP are mixed at a ratio of 2.0 mM:0.18 mM:0.9 mM:0.17 mM:0.17 mM.

The DSPE-PEG-sPDP lipid in the microbubble is used as a crosslinking agent when the microbubble is conjugated to the nanoliposome, thus forming a nanoliposome-microbubble conjugate.

The microbubble may result from bubbling of the mixture of the amphoteric phospholipid, the anionic phospholipid, cholesterol, the cationic phospholipid and the disulfide-group-containing lipid. The inside of the microbubble may be filled with a hydrophobic gas selected from among $SF_6$, $CO_2$, $CF_4$ and $C_3F_8$. The hydrophobic gas is preferably $SF_6$.

The nanoliposome may have a particle size of 100 to 200 nm. If the size of the nanoliposome is less than 10 nm, it is difficult to encapsulate the complex of the Cas9 protein, the guide RNA inhibiting SRD5A2 gene expression and the cationic polymer into the nanoliposome, and the stability thereof may decrease upon in-vivo injection, which is undesirable. On the other hand, if the size thereof exceeds 200 nm, the composition including the nanoliposome may be decreased in stability upon in-vivo injection, which is undesirable. Also, the microbubble may have a particle size of 800 to 1500 nm. Accordingly, the nanoliposome-microbubble conjugate may have a particle size of about 800 to 1500 nm.

The present invention may provide a composition for the amelioration or treatment of hair loss containing the nanoliposome-microbubble conjugate composition. The nanoliposome-microbubble conjugate composition is effective at treating hair loss through SRD5A2 gene therapy.

In the method of preparing the nanoliposome-microbubble conjugate composition according to the present invention, the nanoliposome is prepared, the microbubble is prepared, and the nanoliposome and the microbubble are mixed, thereby yielding a conjugate.

In the preparation of the nanoliposome, upon the preparation of the complex in S1, the Cas9 protein, the guide RNA inhibiting SRD5A2 gene expression and the cationic polymer may be mixed at a molar ratio of 1:1~3:30~70. Here, if the mixing ratio thereof falls out of the above range, it is difficult to obtain the complex. In S1, lecithin, the metal chelating lipid, cholesterol and the cationic phospholipid may be mixed at a molar ratio of 2:0.1~5:0.01~0.5:0.01~0.5. If the mixing ratio thereof falls out of the above range, it is difficult to prepare the lipid that constitutes the nanoliposome. As such, the freezing-thawing in S3 may be repeated 1 to 12 times. When the process of freezing-thawing the lipid

[Chemical Formula 4]

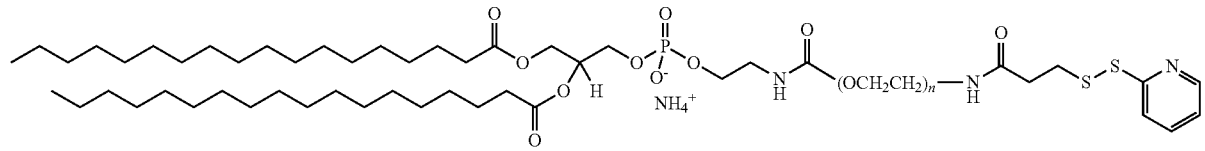

For the preparation of the microbubble, the mixing ratio of the amphoteric phospholipid to the anionic phospholipid to the cholesterol to the cationic phospholipid to the disulfide-group-containing lipid may be 1~3 mM:0.1~0.3 mM:0.5~2 mM:0.1~0.3 mM:0.1~0.3 mM. Here, as the amphoteric phospholipid: anionic phospholipid:cholesterol: cationic phospholipid:disulfide-group-containing lipid, DPPC:DCP:cholesterol:DPPE:sPDP may be used, and preffilm composition is repeated in this way, a nanoliposome dispersion solution having a more uniform size may be formed, and the drug encapsulation efficiency of the nanoliposome may increase. If the number of times the process is repeated exceeds 12, the encapsulation efficiency of the nanoliposome may decrease. Hence, the above process is preferably performed 12 times or less. In S5, the nanoliposome is mixed with the crosslinking agent for 1 to 5 hr, after which the antibody is added thereto and mixed therewith for 1 to 5 hr. In S5, the nanoliposome, the crosslinking agent and the antibody may be bound at a weight ratio of 10~30:1~5:1.

In the nanoliposome prepared in S5, a thiol group may be introduced to the cationic phospholipid in order to realize conjugation to the microbubble. Preferably, 2-iminothiolane hydrochloride is added. When the thiol group is added, only the nanoliposome is recovered, and is then dispersed in a glucose aqueous solution, particularly a glucose aqueous solution having a concentration of 1 to 20% (w/v), and may thus be used for subsequent mixing with the microbubble.

For conjugation of the nanoliposome to the microbubble, the microbubble may be stabilized using at least one solution of a glucose solution, glycerol and propylene glycol in step B during the preparation of the microbubble according to the present invention, and may then be mixed with the nanoliposome. Preferably, a glucose solution is used. Here, the glucose solution may have a concentration of 1 to 20% (w/v). If the concentration of glucose exceeds 20% (w/v), the solution may become viscous, making it impossible to synthesize the microbubble.

Upon the preparation of the nanoliposome according to the present invention, the metal chelating lipid is negatively charged (−), making it difficult to encapsulate the nanoliposome in response to the negative charge (−) of a hybrid of a Cas9 protein and a guide RNA inhibiting SRD5A2 gene expression. Therefore, in order to overcome this problem, the nanoliposome may be more efficiently encapsulated by preparing a complex including the cationic polymer having the positive charge (+).

The present invention may provide a pharmaceutical composition containing the nanoliposome-microbubble conjugate. The pharmaceutical composition of the present invention may be formulated into oral dosage forms, such as powder, granule, tablet, capsule, suspension, emulsion, syrup, and aerosol formulations, as well as formulations for external use, suppositories, and sterile injectable solutions, in accordance with typical individual processes. A carrier, an excipient and a diluent, which may be contained in the pharmaceutical composition, may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. The formulation may be typically prepared using a diluent or excipient such as a filler, an extender, a binder, a wetting agent, a disintegrant, a surfactant, and the like. A solid formulation for oral administration may include tablets, pills, powders, granules, capsules, and the like, and such a solid formulation may be prepared by mixing the composition of the present invention with at least one excipient, for example, starch, calcium carbonate, sucrose, lactose, gelatin, and the like. In addition to the simple excipient, lubricants such as magnesium stearate, talc and the like may be used. An oral liquid formulation may include suspensions, solutions, emulsions, or syrups, and may also include not only simple diluents, such as water or liquid paraffin, but also various excipients, for example, wetting agents, sweeteners, fragrances, and preservatives. A formulation for parenteral administration may include sterilized aqueous solutions, non-aqueous solvents, suspensions, emulsions, freeze-dried preparations and suppositories. As non-aqueous solvents or suspending agents, propylene glycol, polyethylene glycol, vegetable oil such as olive oil, injectable esters such as ethyl oleate and the like may be used. As the base of a suppository, Witepsol, Macrogol, Tween 61, cacao butter, laurin fat, glycerogelatin and the like may be used.

The amount of the pharmaceutical composition according to the present invention, when administered, may vary depending on the age, gender and weight of the subject to be treated, the particular disease or pathological condition for treatment, the severity of the disease or pathological condition, the administration route and the judgment of the prescriber. A dose determination based on these factors will be apparent to those skilled in the art, and the dose typically falls in the range of 0.01 mg/kg/day to about 2000 mg/kg/day. Preferably, the dose is set to the range of 1 mg/kg/day to 500 mg/kg/day. The administration may be carried out once a day or several times a day. The dose does not in any way limit the scope of the present invention.

The pharmaceutical composition of the present invention may be administered to mammals such as mice, livestock, humans, and the like, through various routes. All modes of administration, for example, by oral, intrarectal, intravenous, intramuscular, subcutaneous, intraperitoneal or intracerebroventricular injection, may be considered.

Advantageous Effects

The present invention relates to a nanoliposome-microbubble conjugate, in which a complex of a Cas9 protein, a guide RNA inhibiting SRD5A2 gene expression and a cationic polymer is encapsulated in a nanoliposome and to a composition for the amelioration or treatment of hair loss containing the same. Currently, drugs used for the treatment of hair loss cause serious side effects such as loss of libido or erectile dysfunction, and hair loss progresses again when drug treatment is stopped. However, when the nanoliposome-microbubble conjugate of the present invention is used, the expression of SRD5A2, which induces hair loss, can be fundamentally suppressed, and the treatment of male hair loss can be performed very effectively.

Although Korean Patent No. 10-1710026 discloses a nanoliposome having encapsulated therein a complex of a Cas9 protein targeting a diabetic expression gene, a guide RNA inhibiting SRD5A2 gene expression and a cationic polymer and Korean Patent No. 10-1683463 discloses a microbubble-liposome-melanin nanoparticle complex, a conjugation technique according to the present invention, in which an antibody-bound nanoliposome and a microbubble are conjugated in order to increase the delivery efficiency to genes that cause hair loss or to dermal papilla cells in which the genes are expressed, is not disclosed therein.

BEST MODE

A better understanding of the present invention will be given through the following examples. However, the present invention is not limited to the examples described herein but may be embodied in other forms. Furthermore, the examples are set forth to provide those skilled in the art with an understanding of the spirit of the present invention so that the teachings herein are thorough and complete.

Example 1. Preparation of Guide RNA and Purification of Cas9 Protein

Example 1-1. Preparation of Guide RNA Targeting SRD5A2 Gene

A guide RNA targeting a KRAS gene was prepared through an in-vitro transcription process using T7 RNA polymerase (NEB). To this end, a 140 b.p. DNA template was prepared through a PCR process using, as shown in Table 4 below, a '69-mer forward primer' comprising the T7 promoter sequence and SEQ. ID. NO: 6: GTGTACT-CACTGCTCAATCG, SEQ. ID. NO: 7: AGGGGCC-GAACGCTTGTAAT, SEQ. ID. NO: 8: ACTATATAT-TGCGCCAGCTC, SEQ. ID. NO: 9: CACAGACAT-ACGGTTTAGCT, SEQ. ID. NO: 10: TCCATTCAAT-GATCTCACCG, SEQ. ID. NO: 21: ACAGACA-TGCGGTTTAGCGT, SEQ. ID. NO: 22: CGCGCAA-TAAACCAGGTAAT, SEQ. ID. NO: 23: TCCATT-CAATAATCTCGCCC, SEQ. ID. NO: 24: TCCTGG-GCGAGATTATTGAA, SEQ. ID. NO: 25: AGCCCG-GAGAGGTCATCTAC, corresponding to the 20 b.p. sequence of the SRD5A2 gene, a '20-mer reverse primer' comprising the scaffold sequence to bind to the guide RNA, and a plasmid Cas guide vector (OriGene). This DNA template, an rNTP mixture, a T7 RNA polymerase, and an RNAase inhibitor were subjected to transcription at 37° C. for 2 hr, thus producing a guide RNA, followed by RNA purification, thereby increasing RNA purity.

Figure 17:
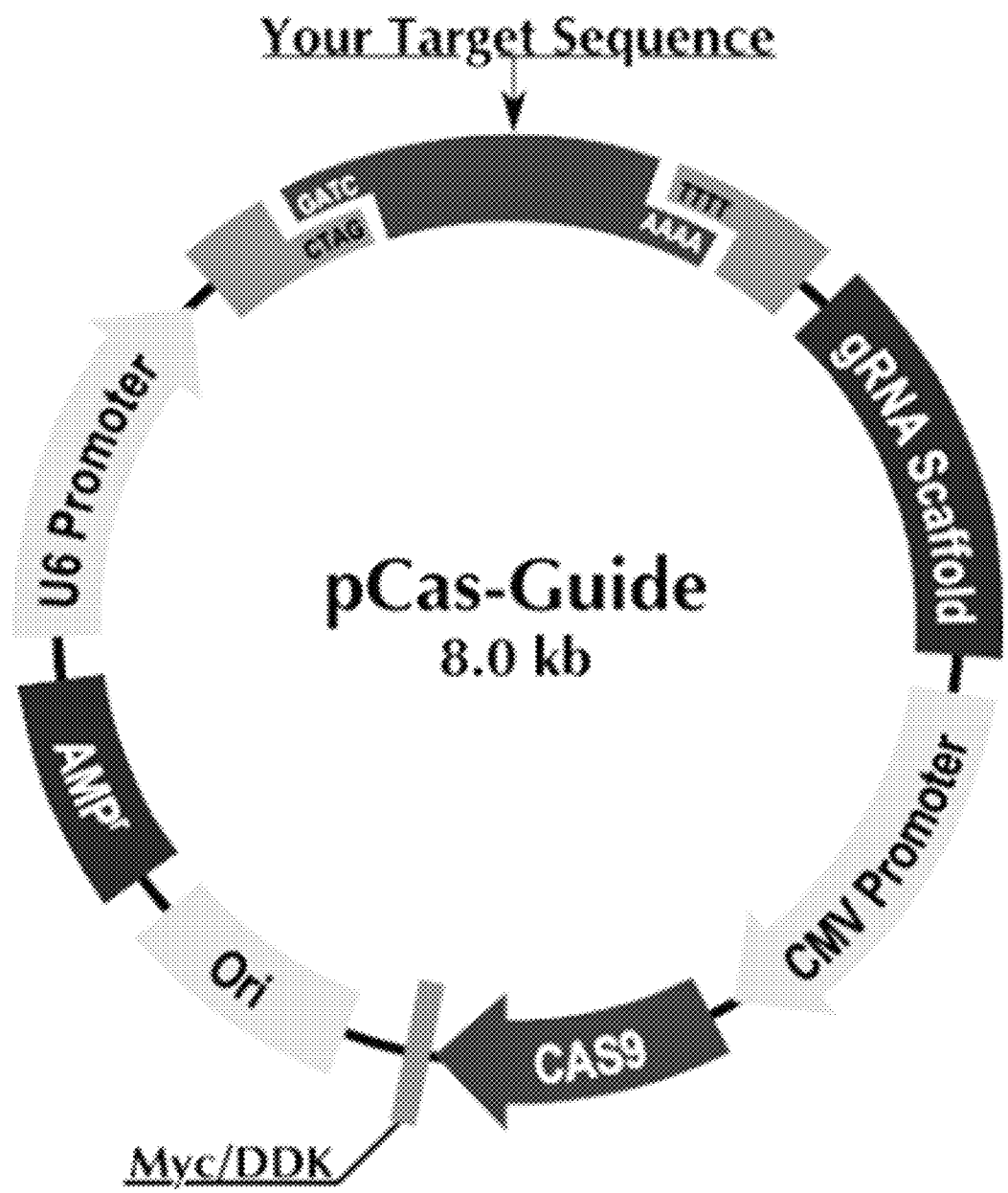
FIG. 17 shows the structure of a plasmid Cas guide vector.

The T7 promoter sequence corresponds to the underlined portion of Table 4 below.
The bold-type sequence of Table 1 is a site that recognizes the SRD5A2 gene, in which the guide RNA is synthesized by recognizing the template (plasmid Cas guide vector) of the scaffold sequence, and the base sequence thereof and the sequence of the final guide RNA are the same (in which T is substituted to U).
GTTTTAGAGCTAGAAATAGCA (SEQ ID NO: 48) after the F primer is a portion of the scaffold sequence.
The plasmid Cas guide vector includes the template of the scaffold sequence.
The structure of the plasmid Cas guide vector used in this test is as shown in FIG. 17. Source: http://www.origene.com/CRISPR-CAS9/Detail.aspx?sku=GE100001

TABLE 4

| | | |
|---|---|---|
| Human SRD5A2 forward primer | sgHNA1 | GCGGCCTCTAATACGACTCACTATAGGGGTGTAC TCACTGCTCAATCGGTTTTAGAGCTAGAAATAGC A (SEQ ID NO: 49) |
| | sgRNA2 | GCGGCCTCTAATACGACTCACTATAGGGAGGGGC CAGACGCTTGTAATGTTTTAGAGCTAGAAATAGC A (SEQ ID NO: 50) |
| | sgRNA3 | GCGGCCTCTAATACGACTCACTATAGGGACTATA TTATGCGCCAGCTCGTTTTAGAGCTAGAAATAGC A (SEQ ID NO: 51) |
| | sgRNA4 | GCGGCCTCTAATACGACTCACTATAGGGCACAGA CATACGGTTTAGCTGTTTTAGAGCTAGAAATAGC A (SEQ ID NO: 52) |
| | sgRNA5 | GCGGCCTCTAATACGACTCACTATAGGGTCCATT CTAAGATCTCACCGGTTTTAGAGCTAGAAATAGC A (SEQ ID NO: 53) |
| Mouse SRD5A2 forward primer | sgRNAm1 | GCGGCCTCTAATACGACTCACTATAGGGACAGAC ATGCGGTTTAGCGTGTTTTAGAGCTAGAAATAGC A (SEQ ID NO: 54) |
| | sgRNAm2 | GCGGCCTCTAATACGACTCACTATAGGGCGCGCA ATAAACCAGGTAATGTTTTAGAGCTAGAAATAGC A (SEQ ID NO: 55) |
| | sgRNAm3 | GCGGCCTCTAATACGACTCACTATAGGGCGCGCA ATAAACCAGGTAATGTTTTAGAGCTAGAAATAGC A (SEQ ID NO: 56) |
| | sgRNAm4 | GCGGCCTCTAATACGACTCACTATAGGGTCCTGG GCGAGATTATTGAAGTTTTAGAGCTAGAAATAGC A (SEQ ID NO: 57) |
| | sgRNAm5 | GCGGCCTCTAATACGACTCACTATAGGGAGCCCG GAGAGGTCATCTACGTTTTAGAGCTAGAAATAGC A (SEQ ID NO: 58) |
| Reverse primer | | AAAAGCACCGACTCGGTGCCA (SEQ ID NO: 59) |

Through the above experiment, the guide RNA having the base sequence of Table 5 below was prepared.

TABLE 5

| | |
|---|---|
| SEQ. ID. NO: 31 (SRD5A2 target) | GUGUACUCACUGCUCAAUCGUUUUAGAGCUAGAA AUAGCAAGUUAAAAUAAGGCUAGUCCGUUAUCAA CUUGAAAAAGUGGCACCGAGUCGGUGCUUUUUU U |
| SEQ. ID. NO: 32 (SRD5A2 target) | AGGGGCCGAACGCUUGUAAUGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 33 (SRD5A2 target) | ACUAUAUAUUGCGCCAGCUCGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 34 (SRD5A2 target) | CACAGACAUACGGUUUAGCUGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 35 (SRD5A2 target) | UCCAUUCAAUGAUCUCACCGGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 36 (SRD5A2 target) | ACAGACAUGCGGUUUAGCGUGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 37 (SRD5A2 target) | CGCGCAAUAAACCAGGUAAUGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 38 (SRD5A2 target) | UCCAUUCAAVAAUCUCGCCCGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 39 (SRD5A2 target) | UCCUGGGCGAGAUUAUUGAAGUUUUAGAGCUAGA AAUAGCAAGUUAAAAUAAGGCUAGUCCGUUAUCA ACUUGAAAAAGUGGCACCGAGUCGGUGCUUUUUU UU |
| SEQ. ID. NO: 40 (SRD5A2 target) | AGCCCGGAGAGGUCAUCUACGUUUUAGAGCUAGA AAUAGCAAGUUAAAAUAAGGCUAGUCCGUUAUCA ACUUGAAAAAGUGGCACCGAGUCGGUGCUUUUUU UU |

The final guide RNA recognizes the base sequences of SEQ. ID. NOS: 11 to 15 of the human SRD5A2 gene as targets, and recognizes the base sequences of SEQ. ID. NOS: 26 to 30 of the mouse SRD5A2 gene as targets.

Example 1-2. Purification of Cas9 Protein

A pET28a/Cas9-Cys plasmid (Addgene plasmid #53261) was transformed into *Escherichia coli* (DH5α) and a Cas9 protein was overexpressed in 0.5 mM IPTG (isopropyl β-D-1-thiogalactopyranoside) at 28° C., and the Cas9-protein-overexpressed *Escherichia coli* was sonicated in a lysis buffer (20 mM Tris-Cl at pH 8.0, 300 mM NaCl, 20 mM imidazole, 1× protease inhibitor cocktail, 1 mg/mL lysozyme). The lysate obtained after sonication was centrifuged to afford a liquid containing the protein. The Cas9 protein was separated from the liquid using a Ni-NTA agarose bead extraction process (elution buffer: 20 mM Tris-Cl at pH 8.0, 300 mM NaCl, 300 mM imidazole, 1×protease inhibitor cocktail). The protein thus separated was dialyzed in a storage buffer (50 mM Tris-HCl at pH 8.0, 200 mM KCl, 0.1 mM EDTA, 1 mM DTT, 0.5 mM PMSF, 20% glycerol) (cutoff 10K), thereby removing imidazole, after which the protein concentration was quantified (using a BCA process).

Figure 18:
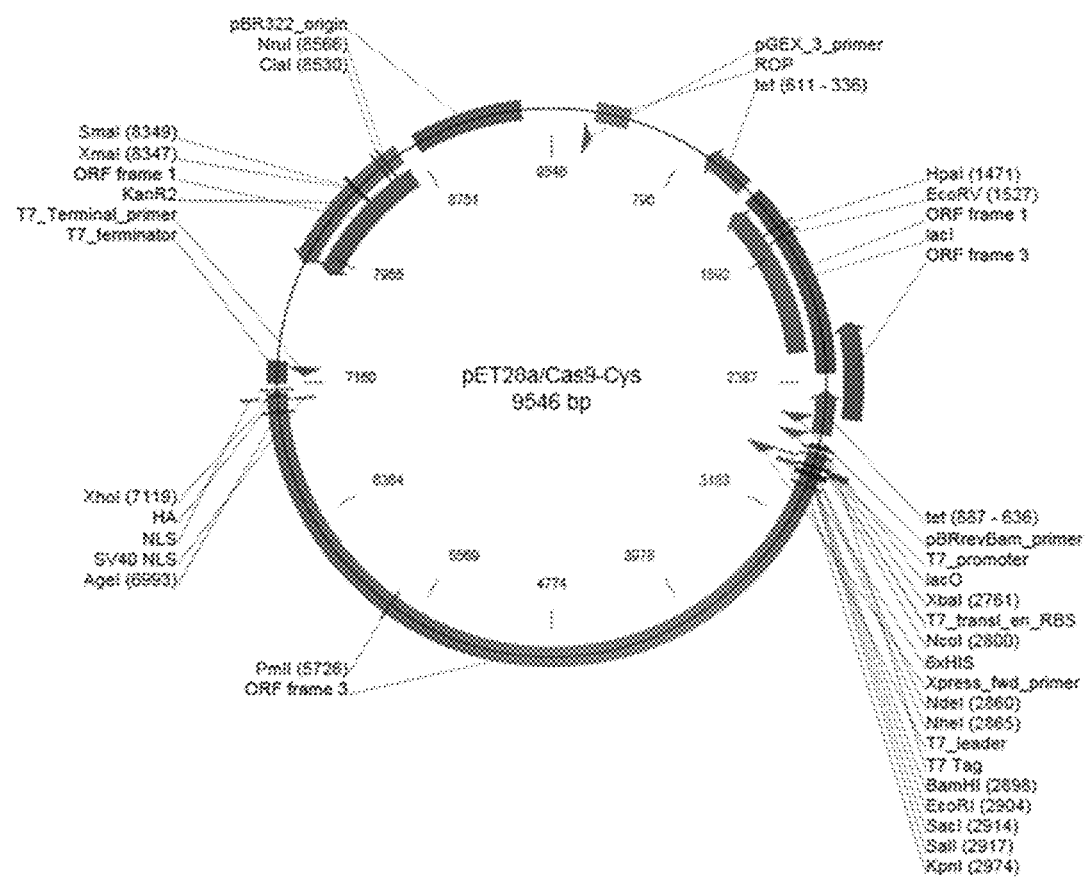
FIG. 18 shows the structure of a pET28a/Cas9-Cys plasmid (Addgene plasmid #53261)

The structure of pET28a/Cas9-Cys plasmid (Addgene plasmid #53261): FIG. 18, Source: Addgene (http://www.addgene.org/)

Example 2. Production of Nanoliposome-Microbubble Conjugate

Example 2-1. Production of Nanoliposome

A complex was prepared by mixing the Cas9 protein prepared in Example 1, guide RNA, and polyethyleneimine at a molar ratio of 1:2:50. Here, as the guide RNA, human SEQ. ID. NO: 31, 32, 33, 34 or 35 including the scaffold sequence (SEQ. ID. NO: 1, 2, 3, 4 or 5 included therein) and mouse SEQ. ID. NO: 36, 37, 38, 39 or 40 (SEQ. ID. NO: 16, 17, 18, 19 or 20 included therein) were used.

Next, lecithin (Sigma Aldrich), DOGS-NTA-Ni lipid (Avanti polar lipids), cholesterol (Sigma Aldrich) and DPPE (Sigma Aldrich) were mixed at a molar ratio of 2:1:0.1:0.05 in chloroform and then made into a lipid film using a rotary evaporator.

The lipid film was added with the Cas9 protein/guide RNA/polyethyleneimine complex and mixed through sonication. A freezing-thawing cycle using liquid nitrogen was repeated five times, and then sonication (probe mode) was performed, thus preparing a uniform nanoliposome composition having a smaller size.

Thereafter, the nanoliposome composition (total amount of lipid: 20.43 mg, and total amount of Cas9 and gRNA: 0.1 mg) precipitated through centrifugation was recovered and mixed with 2.5 mg of sulfo-SMCC (ProteoChem), serving as a linker for antibody binding, at room temperature, that is, 25° C., for 2 hr in PBS.

Next, a purified antibody was provided to bind to the nanoliposome, and the antibody for binding to the nanoliposome was a monoclonal or polyclonal antibody able to recognize endoglin, CD34, keratin 18 and IL-6, which are known to be overexpressed in dermal papilla cells. In particular, an endoglin antibody (Anti-endoglin) was selected, mixed with 2-mercaptoethylamine (Thermo) in 10 mM EDTA at 37° C. for 2 hr, and then purified with a PD-10 desalting column (GE Healthcare) (mixing of endoglin antibody and 2-mercaptoethylamine at a ratio of 1 mg:0.6 mg). As such, the antibody purification process is described through the drawing of FIG. 19 (the antibody comprising the same two Y-shaped chains was added with 2-mercaptoethylamine to afford a half-antibody, which was then purified and bound to the nanoliposome). * The source of FIG. 19: Wu S et al., Highly sensitive nanomechanical immunosensor using half antibody fragments, Anal. Chem., 2014, 86(9), 4271-4277.

Figure 19:
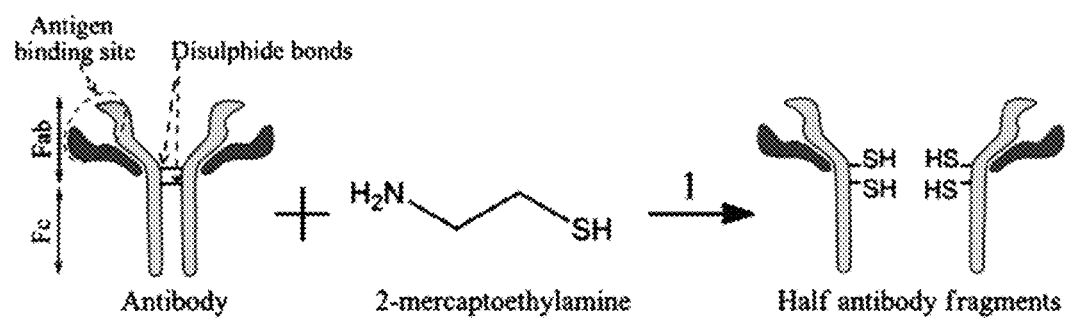
FIG. 19 schematically shows a process of preparing a half-antibody obtained from [Wu S et al].

As seen in FIG. 19, when the half-antibody is made, —SH is produced. Since —NH2 is present in the DPPE lipid of the nanoliposome, it reacts with sulfo-SMCC (linker), and thus the sulfo-SMCC of the nanoliposome and the —SH of the half-antibody bind to each other. In this way, the ability of the nanoliposome to recognize dermal papilla cells can be doubled through the preparation of the half-antibody.

1 mg of the antibody (anti-endoglin) thus purified was mixed with the linker-bound nanoliposome composition at 4° C. for 12 hr, after which the precipitate resulting from centrifugation was recovered, thereby obtaining an antibody-bound nanoliposome able to selectively recognize dermal papilla cells.

In order to conjugate the nanoliposome to the microbubble by introducing a thiol group to DPPE (cationic phospholipid) of the lipid structure of the nanoliposome having the purified antibody bound thereto by the linker, 2-iminothiolane hydrochloride (pH 8.2) (powder phase, added in an amount of 0.5 mg relative to 20.53 mg/mL of nanoliposome) was added, mixed at 25° C. for 2 hr, and centrifuged, and thus the resulting precipitate was recovered and dispersed in a 5% (w/v) glucose aqueous solution.

Example 2-2. Production of Microbubble 15.4 mg of DPPC (1,2-dipalmitoyl-sn-glyerto-3-phosphocholine, Sigma Aldrich), 3.48 mg of cholesterol (Sigma Aldrich), 1 mg of DCP (dicetyl phosphate, Sigma-Aldrich), 1.2 mg of DPPE (1,2-dipalmitoyl-sn-glycero-3-phosphoethanolamine, Sigma Aldrich), and 5 mg of DSPE-PEG-sPDP (1,2-distearoyl-sn-phosphoethanolamine-N-[PDP (polyethylene glycol)], Avanti polar) were mixed in 1 mL of chloroform and then made into a lipid film for microbubble synthesis using a rotary evaporator.

Thereafter, 1 mL of a 5% (w/v) glucose aqueous solution was added thereto and mixed together through sonication. A freezing-thawing cycle using liquid nitrogen was repeated three times, sonication (probe mode) and then filling with an $SF_6$ gas were conducted, thereby preparing a microbubble composition in a dispersed phase.

Example 2-3. Formation of Nanoliposome-Microbubble 1 mL of the nanoliposome (20.53 mg/mL) prepared in Example 2-1 and 0.5 mL of the microbubble (26.08 mg/mL) of Example 2-2 were mixed (at a volume ratio of 2:1), whereby the nanoliposome and the microbubble were dispersed in the glucose aqueous solution.

Thereafter, strong vibration [Mixing frequency: 4500 tr/mn (cpm: $m^3$ per min)] was applied for 15 sec using a machine (Tianjin Iris), thus forming a nanoliposome-microbubble conjugate, which was then refrigerated in the state of being dispersed in a 5% glucose aqueous solution.

The nanoliposome-microbubble conjugate thus obtained is referred to as a 'nanoliposome-microbubble conjugate of Example 2'.

Comparative Example 1. Antibody-Bound Nanoliposome

A nanoliposome (not conjugated with a microbubble) was prepared in the same manner as in Example 2-1, with the exception that only the procedures up to antibody binding were performed and introduction of a thiol group was not carried out, and such a nanoliposome was used as the composition of Comparative Example 1.

Comparative Example 2. Microbubble

A microbubble was prepared in the same manner as in Example 2-2 and was used as the composition (not conjugated with a nanoliposome) of Comparative Example 2.

Comparative Example 3. Nanoliposome

A nanoliposome was prepared in the same manner as in Example 2-1, with the exception that an antibody was not bound thereto, and such a nanoliposome was used as the composition of Comparative Example 3 (antibody-unbound nanoliposome).

Comparative Example 4. Conjugate of Antibody-Bound Nanoliposome Including Scramble Guide RNA and Microbubble A nanoliposome comprising the scramble guide RNA sequence (SEQ. ID. NO: 41: GCACUACCAGAGCUAA-CUCA) as guide RNA was prepared using the nanoliposome preparation method according to the present invention. The scramble guide RNA sequence, which is a sequence that does not bind to any site of the DNA, was prepared for use as a comparative example. The nanoliposome including the scramble guide RNA was introduced with a thiol group (Example 2-2) and conjugated to the microbubble (Example 2-3), thereby preparing a conjugate of the antibody-bound nanoliposome including the scramble guide RNA and the microbubble.

Meanwhile, the nanoliposome-microbubble conjugate of Example 2 having no antibody is considered to be remarkably decreased in targeting effectiveness, and thus was not provided as a comparative example in the present invention.

Test Example 1. Evaluation of Activity and Function of Guide RNA During Preparation of Nanoliposome-Microbubble Conjugate Test Example 1-1. Evaluation of Activity of Guide RNA and Cas9 Protein Dermal papilla cells (DPCs) used for this test are Human Follicle Dermal Papilla Cells (HFDPC), and were purchased from Promocell. These cells were cultured in a 5% $CO_2$ incubator at 37° C. for 24 hr or more in a culture medium obtained by mixing Follicle Dermal Papilla Cell Growth Medium and Follicle Dermal Papilla Cell Growth Medium SupplementMix products of Promocell and were then used for testing.

In order to evaluate the preparation of guide RNA and the purification of Cas9 protein, dermal papilla cells (DPC) were collected, DNA was extracted therefrom, and a template fragment (500 bp) was made through a PCR process using a forward primer: TTGCCCTCCCCACTTTCTGC (SEQ ID NO: 60) and a reverse primer: TCCCACCTTCCGGGTATTGC (SEQ ID NO: 61). Then, the fragment was introduced with the purified Cas9 protein alone or with a combination of purified Cas9 protein and sgRNA3 (SEQ. ID. NO: 33, FIG. 2).

Figure 1:
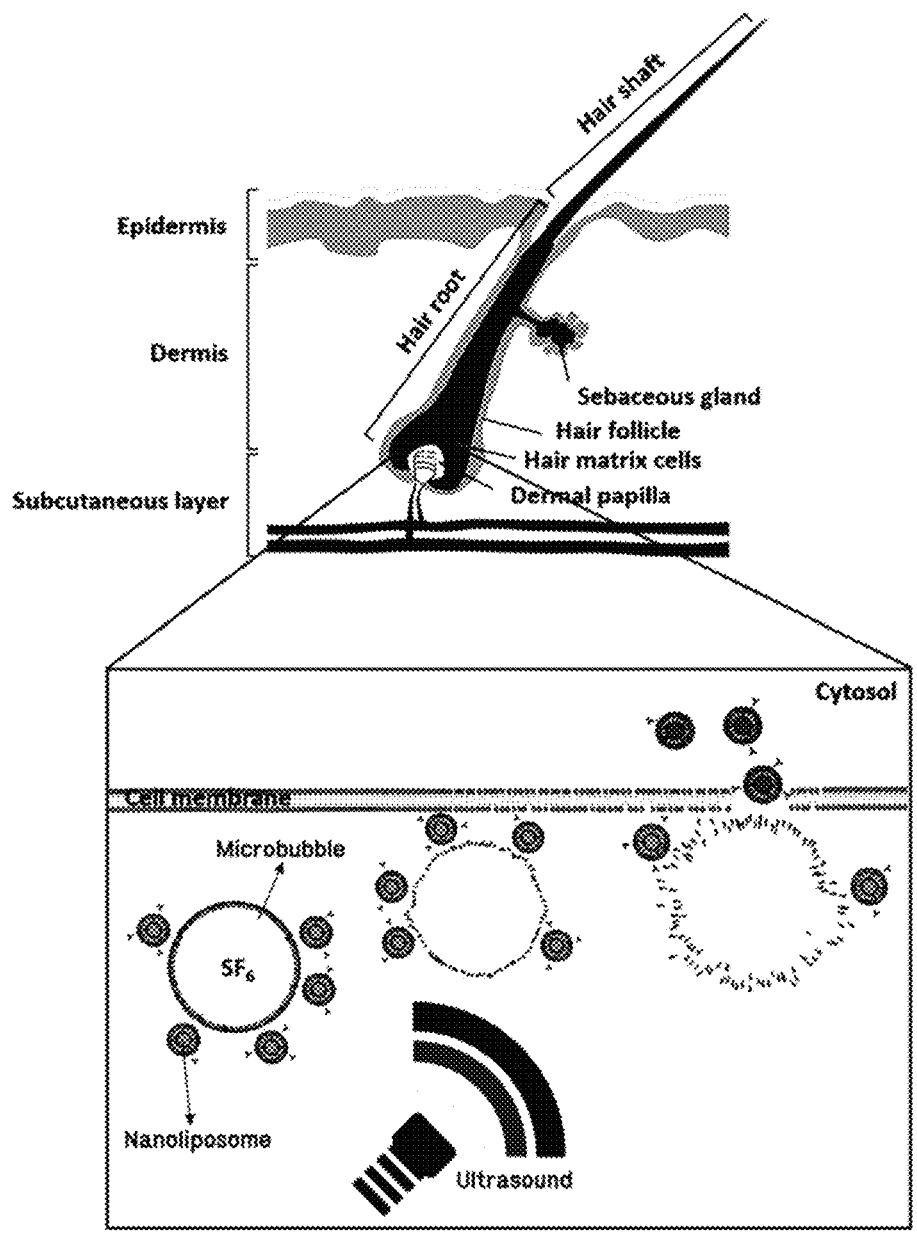
FIG. 1 schematically shows the process by which, when a nanoliposome-microbubble conjugate is delivered to dermal papilla cells (DPCs) and sonication is performed, the cell membrane is perforated and the microbubble collapses, whereby the nanoliposome enters the cells.
Figure 2:
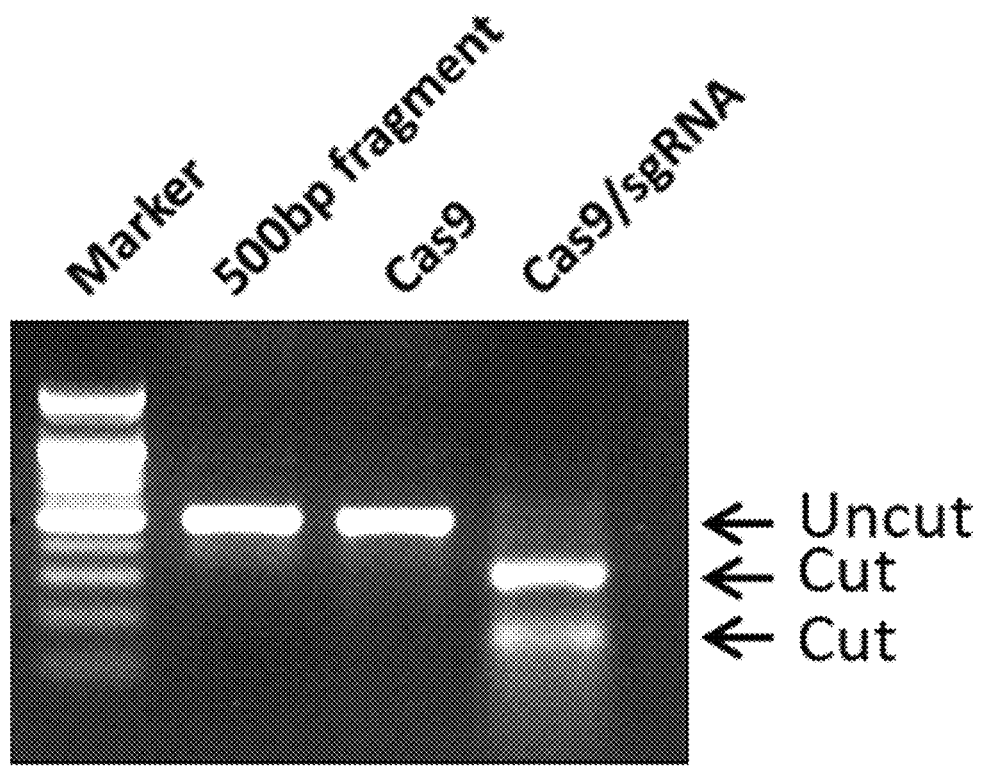
FIG. 2 shows the results of confirming whether the SRD5A2 gene is actually cleaved using a hybrid of in-vitro-transcribed sgRNA and purified Cas9 protein prepared through binding in a laboratory (Cas9/sgRNA hybrid, Cas9-RNP)

With reference to FIG. 2, in the test group using the purified Cas9 protein alone, the fragment was not cleaved with the Cas9 protein due to the absence of guide RNA, and in the test group using the combination of purified Cas9 protein and sgRNA3 (SEQ. ID. NO: 33), the fragment was cleaved with the Cas9 protein.

Test Example 1-2. Evaluation of Size of Nanoliposome-Microbubble Conjugate

Figure 3:
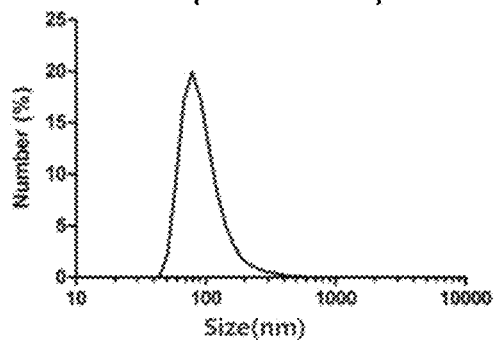
FIG. 3 shows the results of evaluation of size and dispersivity of the nanoliposome of Comparative Example 1, the microbubble of Comparative Example 2 and the nanoliposome-microbubble conjugate of Example 2 through dynamic light scattering (DLS)
Figure 3:
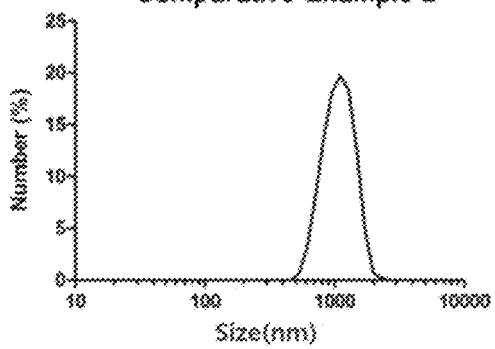
Figure 3:
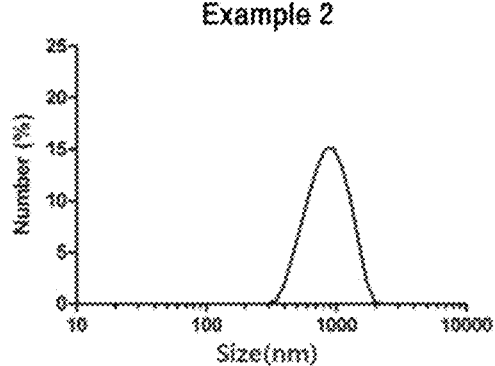

The sizes and surface charges of the nanoliposome, microbubble and nanoliposome-microbubble conjugate prepared in the present invention were measured through dynamic light scattering (DLS). The results based on the inclusion of the guide RNA of SEQ. ID. NO: 33 are shown in Table 6 below and in FIG. 3.

TABLE 6

| Classification | Surface charge (mV) | Average nanoparticle size (nm) |
|---|---|---|
| Example 2 | +2.13 | 955 |
| Comparative Example 1 | +1.78 | 78 |
| Comparative Example 2 | −0.89 | 1106 |

In order to deliver the nanoliposome including the guide RNA into dermal papilla cells, a negative (−) surface charge value has to be changed to a positive charge. With reference to Table 6 and FIG. 3, the nanoliposome of Example 2 has a positive surface charge value. Also, the nanoliposome of Comparative Example 1 and the microbubble of Comparative Example 2 were not greatly changed in size and surface charge compared to the nanoliposome-microbubble conjugate of Example 2.

Figure 4:
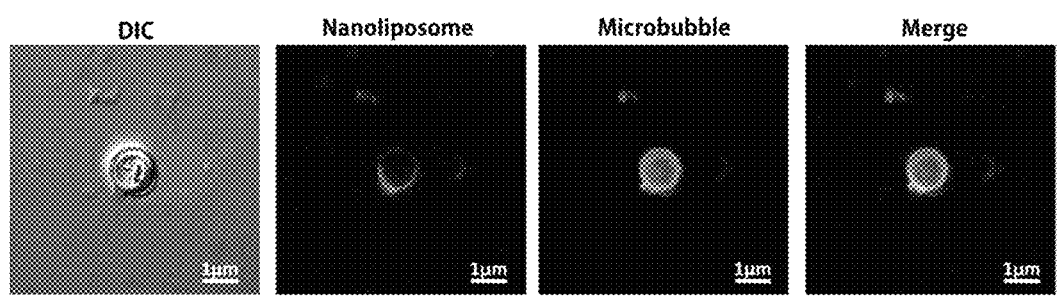
FIG. 4 shows confocal laser scanning microscopy images of the nanoliposome-microbubble conjugate by introducing RITC to the nanoliposome and FITC to the microbubble in order to confirm the conjugation of the nanoliposome and the microbubble in Example 2.

Meanwhile, in order to evaluate whether the composition of Example 2 was provided in the form of a nanoliposome-microbubble conjugate, the state of conjugation of which was maintained, rather than a mixture of a nanoliposome and a microbubble, imaging was performed using confocal laser scanning microscopy. To this end, a RITC (red) fluorescent dye was added upon the preparation of the nanoliposome of Example 2-1 and a FITC (green) fluorescent dye was added upon the synthesis of the microbubble of Example 2-2. Thereby, the nanoliposome-microbubble conjugate of Example 2, ultimately prepared as the nanoliposome-microbubble conjugate in Example 2-3, was analyzed through electron microscopy and fluorescence imaging. The results are shown in FIG. 4, from which the nanoliposome was confirmed to be efficiently conjugated to the microbubble.

Test Example 1-3. Evaluation of Echogenicity of Nanoliposome-Microbubble Conjugate In order to evaluate whether the gas in the microbubble is maintained even after conjugation of the nanoliposome and the microbubble, the echogenicity of the nanoliposome-microbubble conjugate of Example 2 was measured using a clinical sonicator (Philips). Echogenicity is the phenomenon in which an ultrasound image appears white or black depending on the degree of transmission of the ultrasound. Since the nanoliposome contains no gas therein, echogenicity does not occur upon sonication, but the echogenicity of the microbubble containing the gas therein is confirmed. This experiment is based on the efficiency of propagation of ultrasound through the hydrophobic gas in the microbubble because ultrasound radiation travels poorly through the air but is easily transmitted through a liquid or solid. Accordingly, a probe was brought into contact with a test specimen, the ultrasound was generated, and the reflected ultrasound was received to confirm the image.

The mechanical index (MI) of the clinical sonicator for measuring echogenicity was 0.07, and a 2% agarose gel able to contain the nanoliposome-microbubble conjugate was made and measured with a 5~12 MHz rectangular ultrasonic probe.

Figure 5:
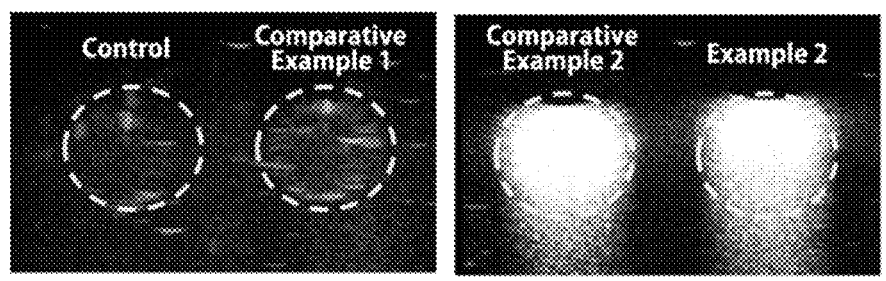
FIG. 5 shows the results of echogenicity in order to confirm whether the hydrophobic gas is maintained in the nanoliposome of Comparative Example 1, the microbubble of Comparative Example 2 and the nanoliposome-microbubble conjugate of Example 2.
Figure 5:
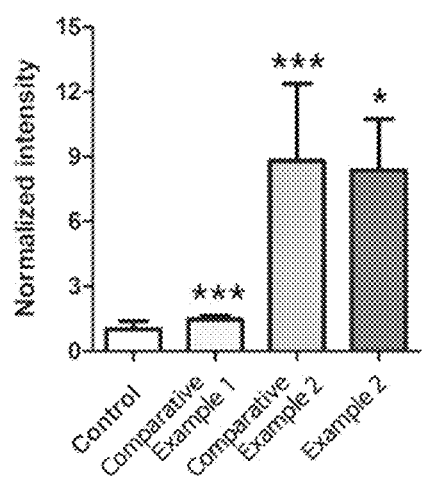

The results thereof are shown in FIG. 5. When comparing the microbubble of Comparative Example 2 with the nanoliposome-microbubble conjugate of Example 2, there was no change in echogenicity, and thus it can be concluded that the nanoliposome-microbubble conjugate of Example 2 was configured such that the nanoliposome was efficiently conjugated to the microbubble containing therein $SF_6$ gas in intact form.

Test Example 2. Measurement of SRD5A2 Expression and Activity

Test Example 2-1. Comparison of SRD5A2 Expression Efficiency of Guide RNA

In order to compare the efficiencies of sgRNA 1, 2, 3, 4 and 5 (SEQ. ID. NOS: 1, 2, 3, 4 and 5) in dermal papilla cells (DPCs), the pCas plasmid (the pCas-Guide plasmid of Example 1-1) was introduced with SEQ. ID. NOS: 6, 7, 8, 9 and 10, and the dermal papilla cells were treated therewith.

The treated cells were collected, total RNA was extracted therefrom using TRIzol (Invitrogen), and cDNA was synthesized using SuprimeScript RT premix 2× (GeNetBio).

Real-time PCR for measuring mRNA expression of SRD5A2 was measured using SYBR green 2× Premix (Applied Biosystems) and an AB Step One Plus real-time PCR system (Applied Biosystems). As such, the base sequences of primers used for the detection were as follows.

SRD5A2 sense: GGCCTCTTCTGCGTAGATTA (SEQ ID NO: 44)

SRD5A2 antisense: CACCCAAGCTAAACCGTATG (SEQ ID NO: 45)

GAPDH sense: GCACCGTCAAGGCTGAGAA (SEQ ID NO: 46)

GAPDH antisense: AGGGATCTCGCTCCTGGAA (SEQ ID NO: 47)

Figure 6:
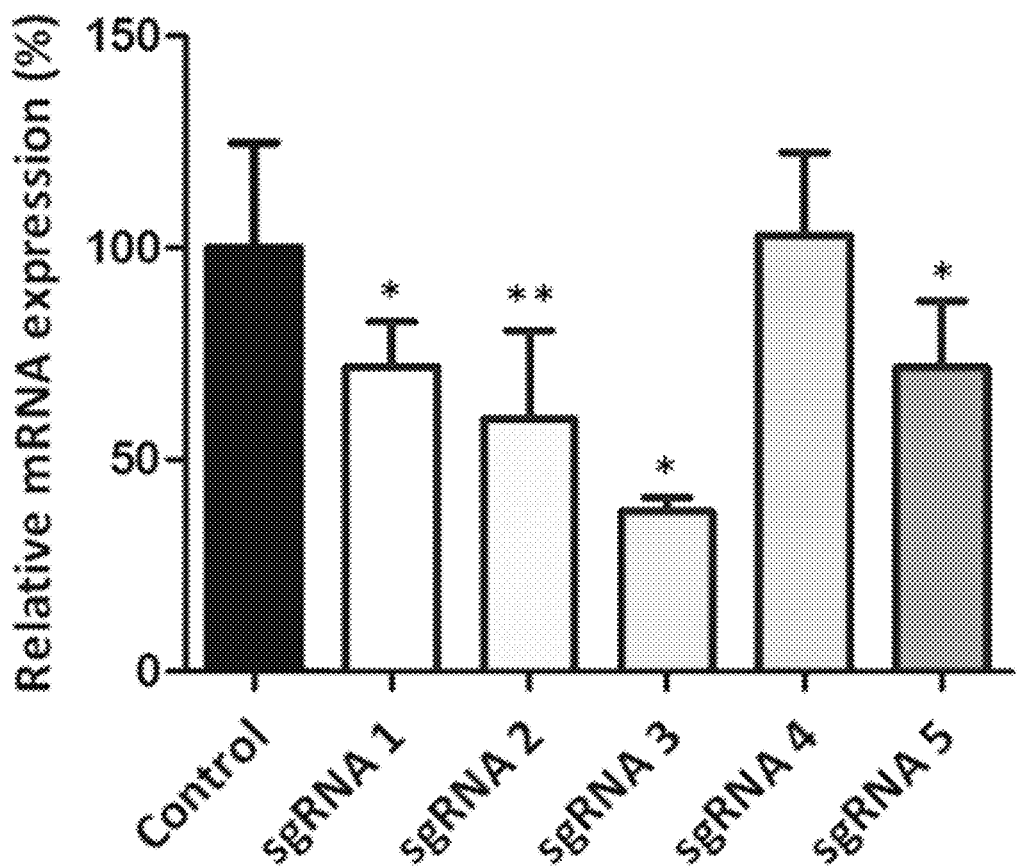
FIG. 6 shows the results of measurement of efficiency of the single-stranded guide RNA according to the present invention (sgRNA 1~5, SEQ. ID. NOS: 1~5 in order) through introduction thereof into the plasmid system and then mRNA expression of SRD5A2 in dermal papilla cells.

The above results are shown in FIG. 6. Based on the results of comparison of efficiency of sgRNA in DPCs, sgRNA 3 (SEQ. ID. NO: 3) most efficiently reduced the SRD5A2 mRNA expression, and thus these including the guide RNA of SEQ. ID. NO: 3 were used in all subsequent tests.

Figure 7:
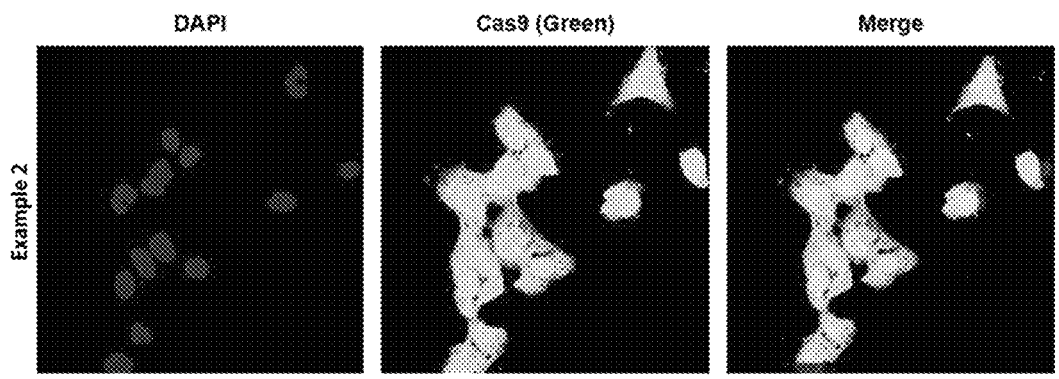
FIG. 7 shows confocal laser scanning microscopy images after treatment of dermal papilla cells with the nanoliposome-microbubble conjugate and then immunostaining with an antibody to Cas9 in order to confirm whether the nanoliposome-microbubble conjugate of the present invention is introduced into dermal papilla cells.

Test Example 2-2. Evaluation of Introduction of Nanoliposome-Microbubble Conjugate into Dermal Papilla Cells In order to evaluate whether the nanoliposome-microbubble conjugate of Example 2 was introduced into dermal papilla cells, DPCs were treated for 2 hr with the nanoliposome-microbubble conjugate of Example 2 at a concentration of Cas9:gRNA (24.7 μg:8.6 μg-24.7 μg of Cas9 and 8.6 μg of gRNA in total broth), followed by immunostaining with an antibody to Cas9. The confocal laser scanning microscopy images thereof are shown in FIG. 7. For immunostaining, the intracellular Cas9 protein was labeled using a Cas9 primary antibody (Rabbit) and then a secondary antibody CFL-488 and was then imaged by confocal laser scanning microscopy. The results based on the inclusion of the guide RNA of SEQ. ID. NO: 33 are shown in FIG. 7.

In FIG. 7, DAPI shows the DNA-stained image, Cas9 shows the CFL-4880-stained image of the Cas9 protein, and Merge shows the image of combination thereof. With reference to FIG. 6, the Cas9 protein can be seen to be efficiently injected into the nuclei of dermal papilla cells due to treatment with the nanoliposome-microbubble conjugate of Example 2.

Figure 8A:
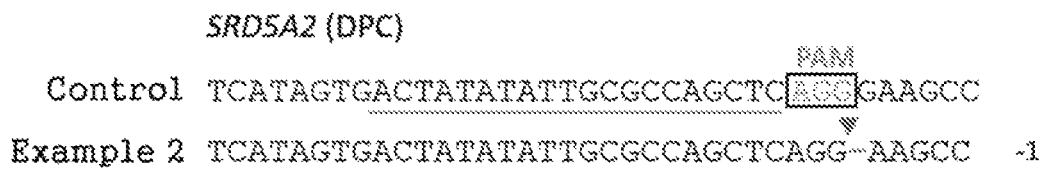
FIG. 8A schematically shows the cleavage of one base sequence after the PAM structure in the SRD5A2 gene through treatment of dermal papilla cells with the nanoliposome-microbubble of Example 2 according to the present invention (tcatagtgac tatatattgc gccagctcag ggaagcc (SEQ ID NO: 42); and tcatagtgac tatatattgc gccagctcag gaagcc (SEQ ID NO: 43))

Meanwhile, the position of the human genomic DNA recognized by the guide RNA of SEQ. ID. NO: 3 is shown in FIG. 8A (green underline). With reference thereto, by virtue of the nanoliposome-microbubble conjugate according to the present invention, 20 base sequences were recognized by the guide RNA, and the PAM (protospacer adjacent motif) (AGG sequence) site was cleaved with the Cas9 protein, whereby the cleavage of one DNA sequence during self-repair of the cleaved DNA was confirmed (the genomic DNA was directly extracted from the cells treated with the nanoliposome-microbubble of Example 2, and the position of the cleaved sequence shown in FIG. 8A was identified through a sequencing service provided by Bionia Inc.).

Test Example 2-3. Determination of SRD5A2 Expression—Measurement of mRNA Expression Level The dermal papilla cells were treated for 2 hr with the nanoliposome-microbubble prepared in the present invention at a concentration of Cas9:gRNA (24.7 μg:8.6 μg), after which total RNA was extracted from the collected cells using TRIzol (Invitrogen), and cDNA was synthesized using SuprimeScript RT premix 2× (GeNetBio).

Real-time PCR for measuring mRNA expression of SRD5A2 was performed using SYBR green 2× Premix (Applied Biosystems) and an AB Step One Plus real-time PCR system (Applied Biosystems). The base sequences of primers used for the detection were as follows.

SRD5A2 sense: GGCCTCTTCTGCGTAGATTA (SEQ ID NO: 44)
SRD5A2 antisense: CACCCAAGCTAAACCGTATG (SEQ ID NO: 45)
GAPDH sense: GCACCGTCAAGGCTGAGAA (SEQ ID NO: 46)
GAPDH antisense: AGGGATCTCGCTCCTGGAA (SEQ ID NO: 47)

Figure 8B:
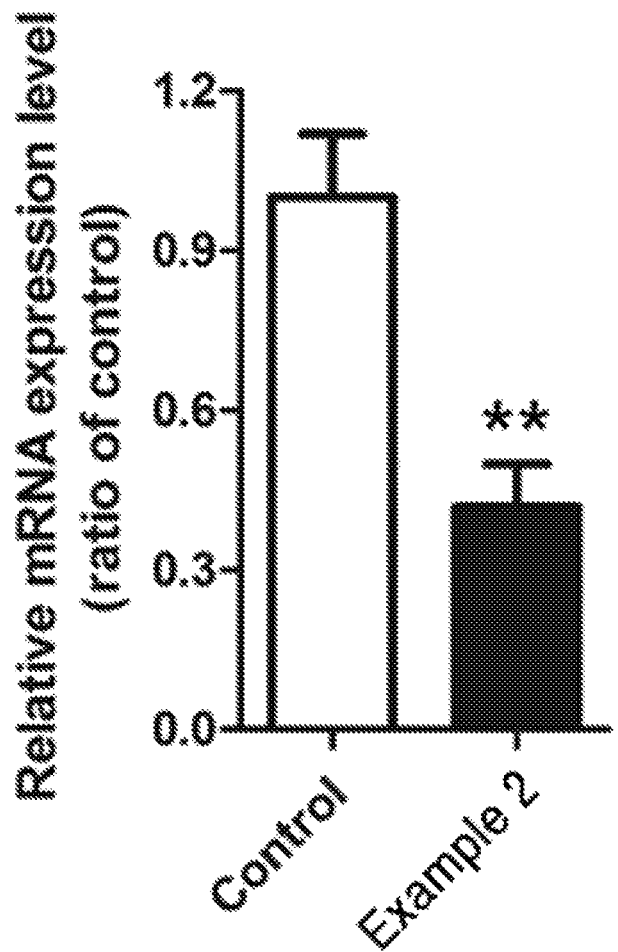
FIG. 8B shows the results of evaluating the effect of inhibiting SRD5A2 mRNA expression after treatment of cells with the nanoliposome-microbubble of Example 2 and then sonication.

The above results are shown in FIG. 8B, from which the mRNA expression of SRD5A2 can be confirmed to be remarkably decreased in dermal papilla cells due to the treatment with the nanoliposome-microbubble conjugate of Example 2.

Test Example 2-4. Determination of SRD5A2 Expression—Measurement of Protein Expression Level The nanoliposome-microbubble conjugate of Example 2 was treated under the same conditions as the mRNA expression test, with the exception that the number of times the treatment with the nanoliposome-microbubble conjugate was repeated was varied in the range from 1 to 5 per day. The dermal papilla cell (DPC) test groups were collected, and these cells were treated with a RIPA buffer (Sigma) and the protein was extracted therefrom, after which the expression of SRD5A2 protein was identified using an SRD5A2 ELISA kit (Antibodies-online). Here, the compositions of Comparative Examples 1 to 4 were subjected to the same test.

Figure 9:
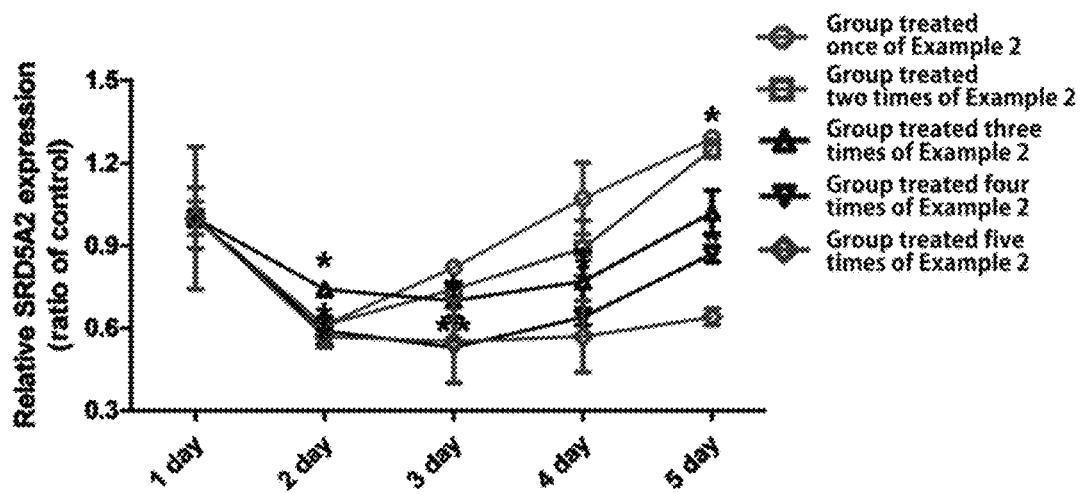
FIG. 9 shows the results of evaluation of the extent of SRD5A2 protein expression after treatment of dermal papilla cells with the nanoliposome-microbubble conjugate of Example 2 according to the present invention.

Consequently, as the number of times the process using the composition of Example 2 according to the present invention is repeated increases, the SRD5A2 protein expression level decreases, and this decrease is maintained for 5 days or more, unlike the group (control) not treated with the nanoliposome-microbubble conjugate, as is apparent from Table 7 below and FIG. 9.

TABLE 7

| Classification | SRD5A2 protein expression (fold) on the $5^{th}$ day of cell treatment |
| --- | --- |
| Non-treated group | 1.00 |
| Group treated 5 times of Example 2 | 0.43 |
| Group treated 5 times of Comparative Example 1 | 0.75 |
| Group treated 5 times of Comparative Example 2 | 0.99 |
| Group treated 5 times of Comparative Example 3 | 0.85 |
| Group treated 5 times of Comparative Example 4 | 0.98 |

Test Example 3. Measurement of Cell Viability and Increment Rate

Test Example 3-1. Live/Dead Cells

The dermal papilla cells were repeatedly treated for 2 hr with the nanoliposome-microbubble conjugate finally obtained in Example 2 at a concentration of Cas9:gRNA (24.7 μg:8.6 μg-24.7 μg of Cas9 and 8.6 μg of gRNA in total broth) once a day for a total of five days (treatment standard once a day, the same conditions as in Test Example 2-4). Thereafter, in order to induce the apoptosis conditions of dermal papilla cells causing hair loss, the dermal papilla cells used for testing were treated with 2 μm Calcein AM (Calcein acetoxymethyl ester) and 4 μM EthD-1 (Ethidium homodimer-1) at 25° C. for 30 min using a new medium.

Cell survival and apoptosis were evaluated by subjecting the cells to fluorescence staining using a LIVE/DEAD Viability/Cytotoxicity kit (Thermo) and imaging using confocal laser scanning microscopy. The living cells show green fluorescence by recognizing the activity of esterase in the cells by Calcein AM, and EthD-1 (Ethidium homodimer-1)

penetrates the damaged cell membrane of the dead cells and thus enters the cells and bind to the nucleic acid, thus showing red fluorescence.

Figure 10:
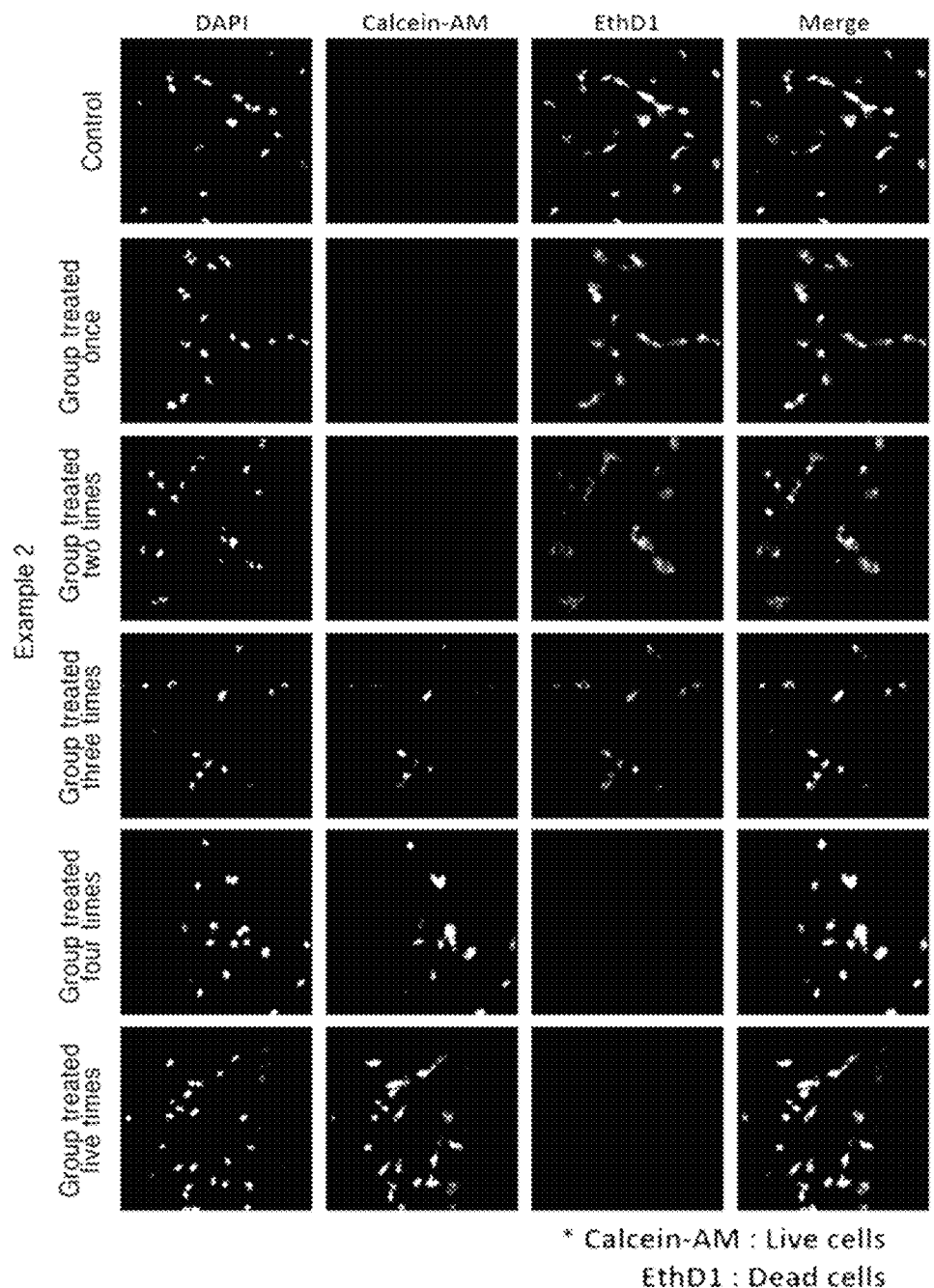
FIG. 10 shows confocal laser scanning microscopy images of the state of survival of dermal papilla cells when dermal papilla cells are pretreated with the nanoliposome-microbubble conjugate of Example 2 according to the present invention and then treated with testosterone.

The results are shown in FIG. 10, and cell viability can be seen to increase depending on the number of times the treatment with the nanoliposome-microbubble conjugate of Example 2 is repeated.

Test Example 3-2. Measurement of Cell Viability

Cell viability was measured through WST-1 assay (EZ-cytox Cell Viability Assay Kit). DPCs were cultured at a density of $1 \times 10^4$/well in a 96-well plate for 24 hr, and were then treated with the nanoliposome-microbubble conjugate of each of Example 3 and Comparative Examples 3, 4, 5 and 6, after which the culture medium was replaced with a new medium containing testosterone at each of different concentrations (200 μM, 400 μM), and after 24 hr, a WST-1 reagent was added thereto. The WST-1 reagent was added in an amount of 10% of the culture broth, and after 1 hr, absorbance was measured at 460 nm and thus the cell survival and proliferation were compared with a control (non-treated group). Cell survivals were evaluated at an interval of 24 hr for 5 days after treatment with the nanoliposome.

Figure 11A:
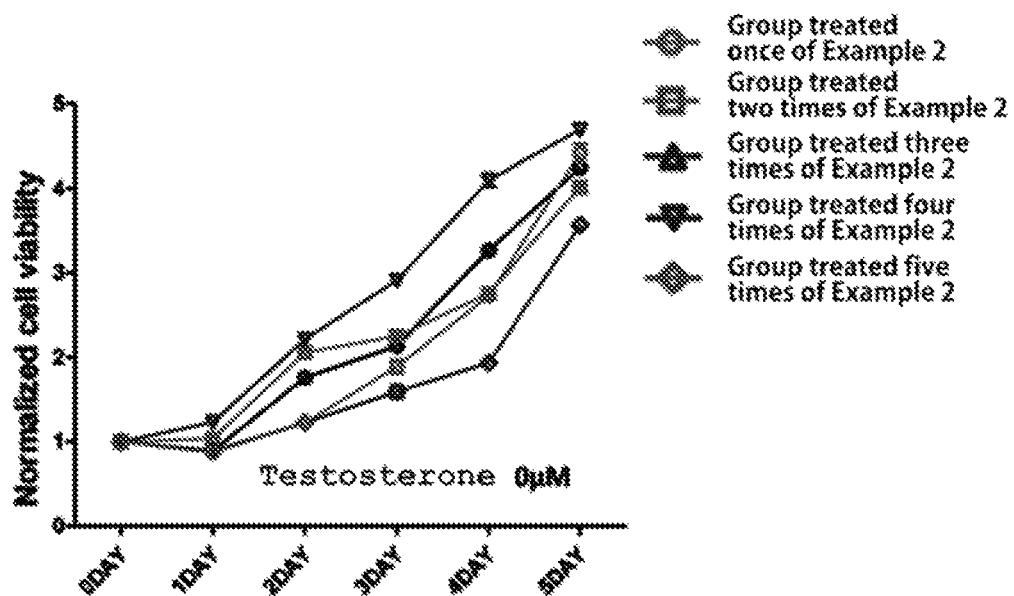
FIGS. 11A, 11B and 11C show the results of WST-1 assay of the cell survival and proliferation when dermal papilla cells are pretreated with the nanoliposome-microbubble conjugate of Example 2 according to the present invention and then treated with testosterone.
Figure 11B:
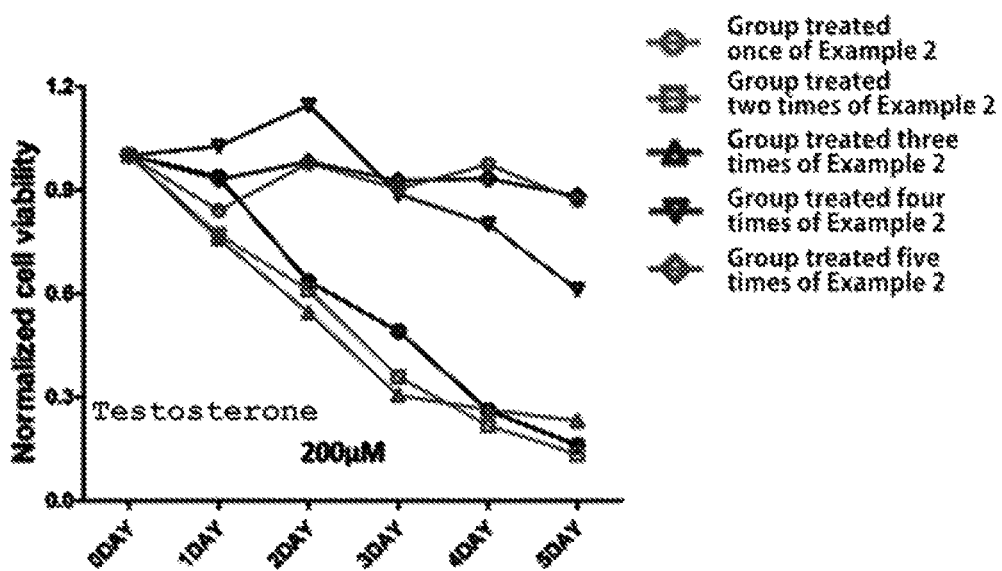
Figure 11C:
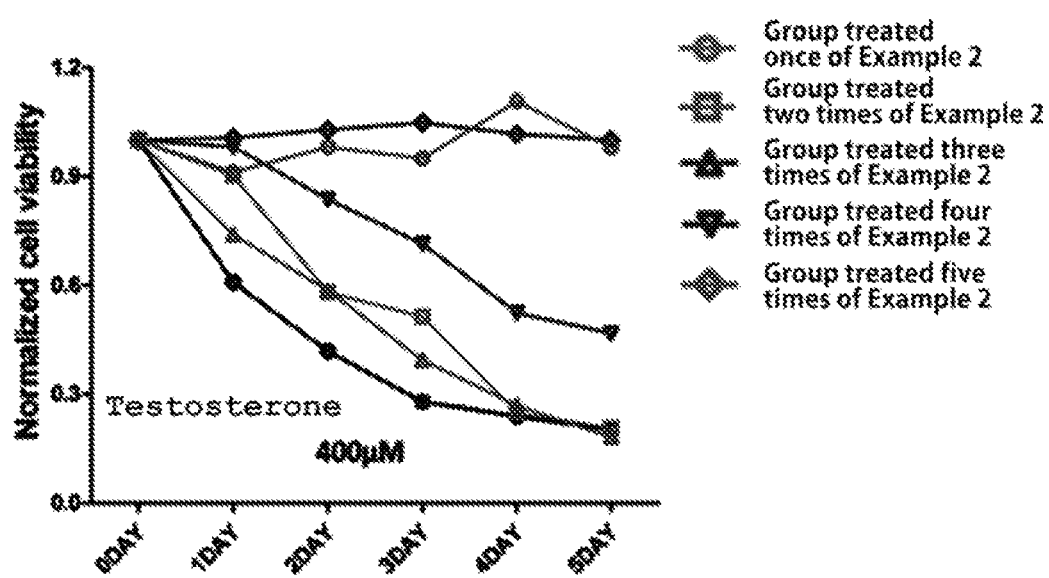

Here, FIG. 11A shows the results of the cell test groups treated with the nanoliposome-microbubble conjugate alone, in which the cells were well grown without toxicity of the nanoliposome-microbubble conjugate, and FIGS. 11B and 11C show the results of the cell test groups after treatment with the nanoliposome-microbubble conjugate of Example 2 and then with 200~300 μM testosterone, in which cell survival and proliferation were remarkably increased depending on the number of times the process using the nanoliposome-microbubble conjugate was repeated. These results indicate that the nanoliposome-microbubble conjugate of Example 2 of the present invention can effectively inhibit testosterone-mediated apoptosis in cells.

Test Example 4. Measurement of Amount of Testosterone Converted into Dihydrotestosterone Whether testosterone was actually converted into dihydrotestosterone (DHT) was evaluated after editing of the SRD5A2 gene in the cells with the nanoliposome-microbubble conjugate of Example 2 of the present invention. The cells were treated with the nanoliposome-microbubble conjugate in the same manner as in Test Example 3-2, and were then treated for 24 hr using a new medium containing testosterone (0 to 400 μM).

Figure 12:
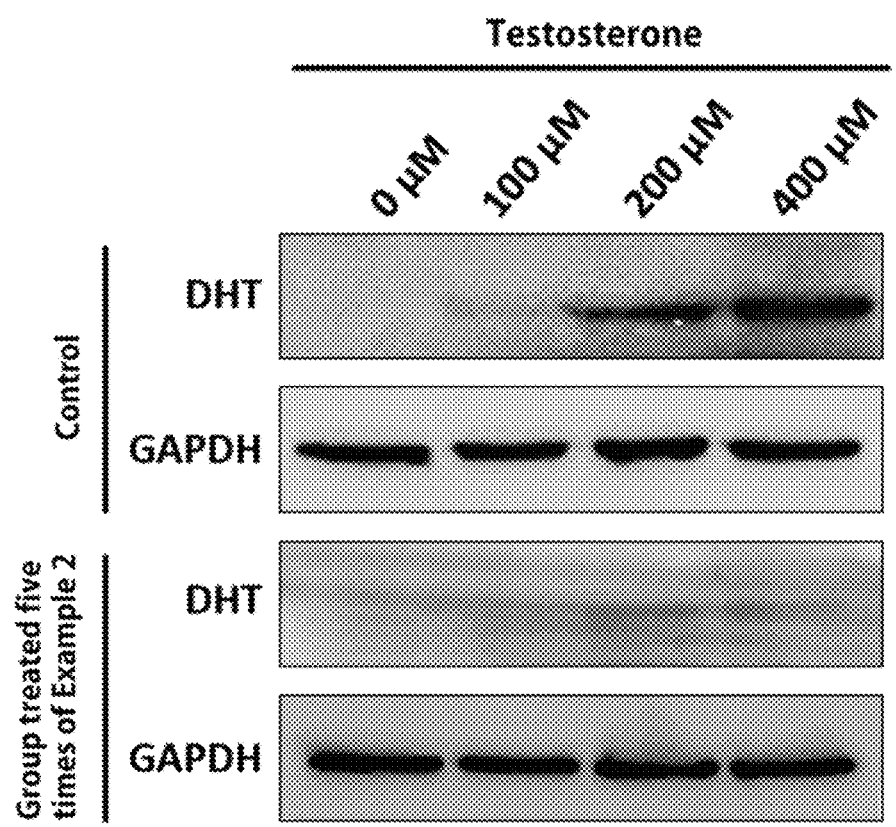
FIG. 12 shows the results of western blotting of the extent of conversion into dihydrotestosterone upon treatment of dermal papilla cells with testosterone after pretreatment with the nanoliposome-microbubble conjugate of Example 2 according to the present invention.

The results are shown in FIG. 12, in which the expression level of dihydrotestosterone was increased in proportion to the treatment concentration of testosterone in a control (non-treated group), but in the group treated with the nanoliposome-microbubble conjugate of Example 2, even when the treatment concentration of testosterone was high, the expression of the dihydrotestosterone protein was not relatively increased. Accordingly, the composition of the present invention can be concluded to inhibit the progression of hair loss.

Test Example 5. Measurement of Caspase-3 Activity

Caspase-3 activity was measured using a caspase-3 assay kit (Cell Signaling). As in previous tests, dermal papilla cells were treated with the nanoliposome-microbubble conjugate of Example 2 for 1 to 5 days, and were then further treated for 24 hr using a new medium containing testosterone (200 μM, 400 μM). Thereafter, protein was extracted from the cells, and the extracted protein was mixed with 200 μL of a 1× assay buffer A and a substrate solution B and reacted at 37° C. for 30 min. After the reaction, fluorescence values were measured at an excitation wavelength of 380 nm and an emission wavelength of 440 nm to thus determine caspase-3 activity.

Figure 13:
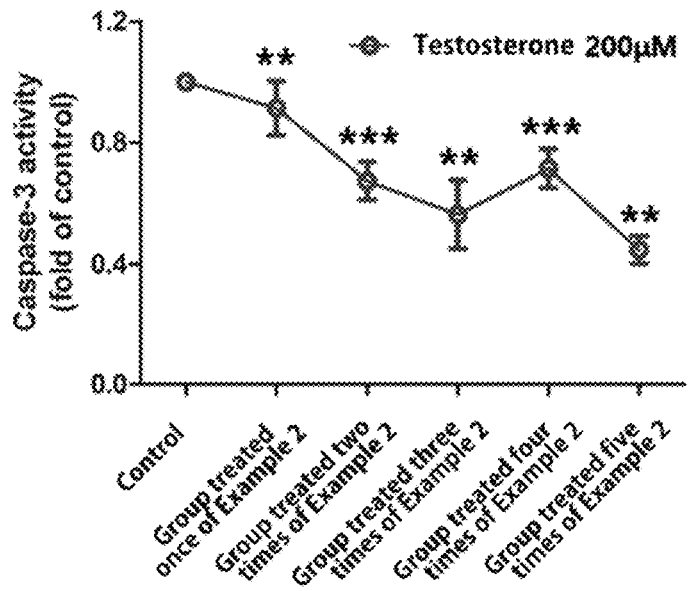
FIG. 13 shows the results of measurement of caspase-3 activity in order to evaluate apoptosis upon treatment of dermal papilla cells with testosterone after pretreatment with the nanoliposome-microbubble conjugate of Example 2.
Figure 13:
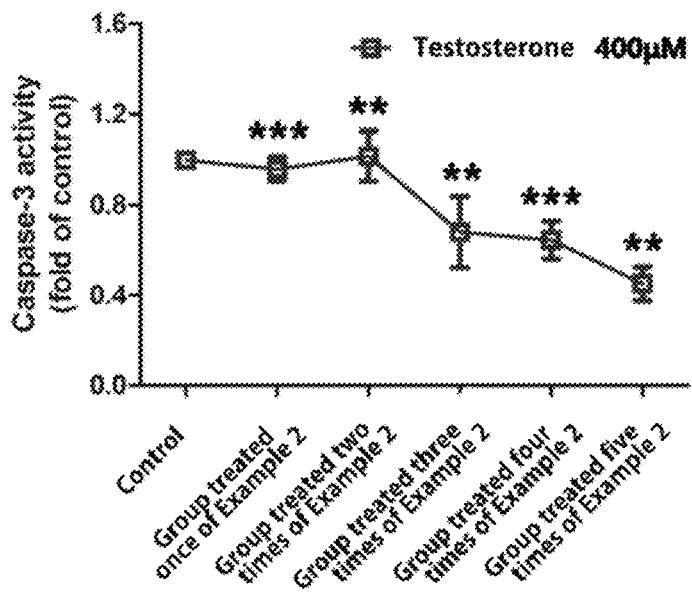

The above results are shown in FIG. 13, from which the caspase-3 activity can be concluded to be significantly decreased depending on the number of times the process using the nanoliposome-microbubble conjugate of Example 2 is repeated upon treatment with testosterone after editing of the SRD5A2 gene.

Test Example 6. Evaluation of Effect of Nanoliposome-Microbubble Conjugate on Inhibiting Hair Loss in Mouse Model Test Example 6-1. Evaluation of Activity of Guide RNA in Mouse Dermal Tissue DNA In order to compare the efficiencies of sgRNA m1, m2, m3, m4 and m5 (SEQ. ID. NOS: 16, 17, 18, 19 and 20) in cells of mouse dermal papilla tissue, mouse dermal tissue was obtained and DNA was extracted therefrom. The extracted DNA was subjected to a PCR process using a forward primer: CTCTTTGGACTATTTTGTGGCTT (SEQ ID NO: 62) and a reverse primer: AAGACTGGGAACAT-TTGGTTTGT (SEQ ID NO: 63) for sgRNA m1 and m2, a forward primer: GGCAGGAAGCCCCTCAGGGAGAT (SEQ ID NO: 64) and a reverse primer: AATGTGACCGGCTGCTTCAAGTT (SEQ ID NO: 65) for sgRNA m3 and m4, and a forward primer: AACC-CAAAACCAAACACAAAACC (SEQ ID NO: 66) and a reverse primer: GGGTCATAGACATGTGCACCATG (SEQ ID NO: 67) for sgRNA 5 to afford each template fragment (500 bp). Then, the purified Cas9 protein was added thereto alone or in combination with sgRNA m1, m2, m3, m4 and m5 (SEQ. ID. NOS: 36, 37, 38, 39 and 40).

Figure 14:
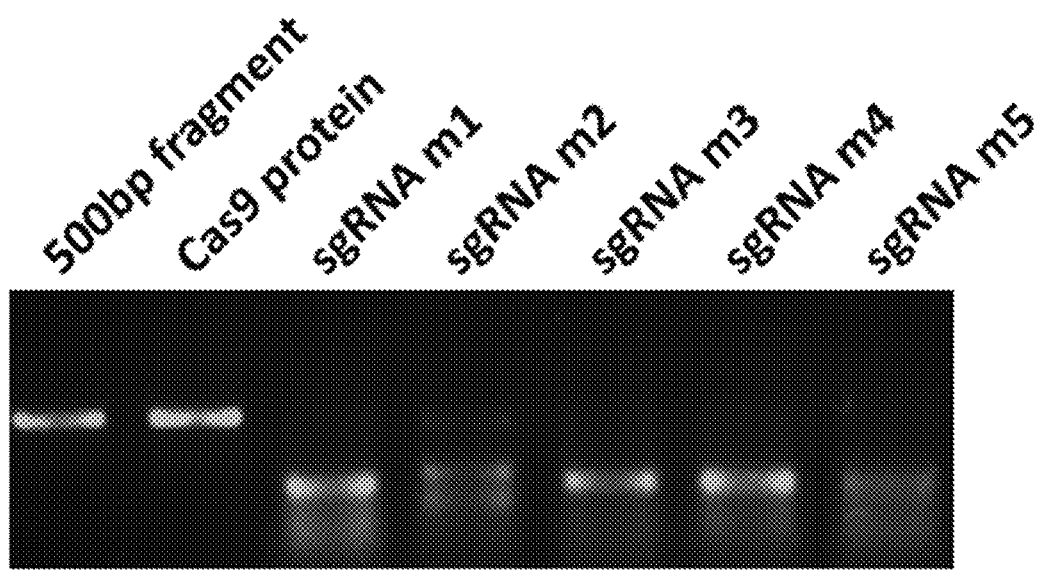
FIG. 14 shows the results of measurement of the activity of a hybrid of a Cas9 protein and a guide RNA by mixing DNA extracted from mouse dermal tissue with a Cas9 protein and a single-stranded mouse guide RNA (sgRNA m1~5: SEQ. ID. NOS: 36~40 in order)

With reference to FIG. 14, in the test group using the purified Cas9 protein alone, the fragment was not cleaved with the Cas9 protein due to the absence of guide RNA, and in the test groups using the combinations of purified Cas9 protein and sgRNA m1, m2, m3, m4 and m5 (SEQ. ID. NOS: 36, 37, 38, 39 and 40), the fragment was cleaved with the Cas9 protein. In particular, the efficiency of sgRNA m1 (SEQ. ID. NO: 36) was evaluated to be the greatest, and thus those including the guide RNA of SEQ. ID. NO: 36 were used in all subsequent mouse tests.

Test Example 6-2. Evaluation of Efficiency as Therapeutic Agent for Ameliorating and Treating Hair Loss in Mouse The hair of the back of each of 6-week-old mice (C57BL/6J) was epilated using an animal epilator (Philips) and hair removal cream (Veet), and in control 2 and test groups 1, 2 and 3, testosterone (30 μg/mL) dissolved in a mixed solution (3:7 (v:v)) of propylene glycol and ethanol was applied thereon every day and thus an environment similar to human hair loss was made. In control 1, no treatment was performed after epilation. In test groups 1, 2 and 3, the nanoliposome-microbubble conjugate (200 μL, nanoliposome-microbubble conjugated at a ratio of 2:1 and dispersed) of Example 2 of the present invention was applied in an amount of 200 μL each using a plastic spatula on the entire epilated back of each mouse, and after 3 min, sonication was performed using a medical sonicator. Treatment with the conjugate of Example 2 was performed once in test group 1, three times in test group 2, and five times in test group 3.

Figure 15:
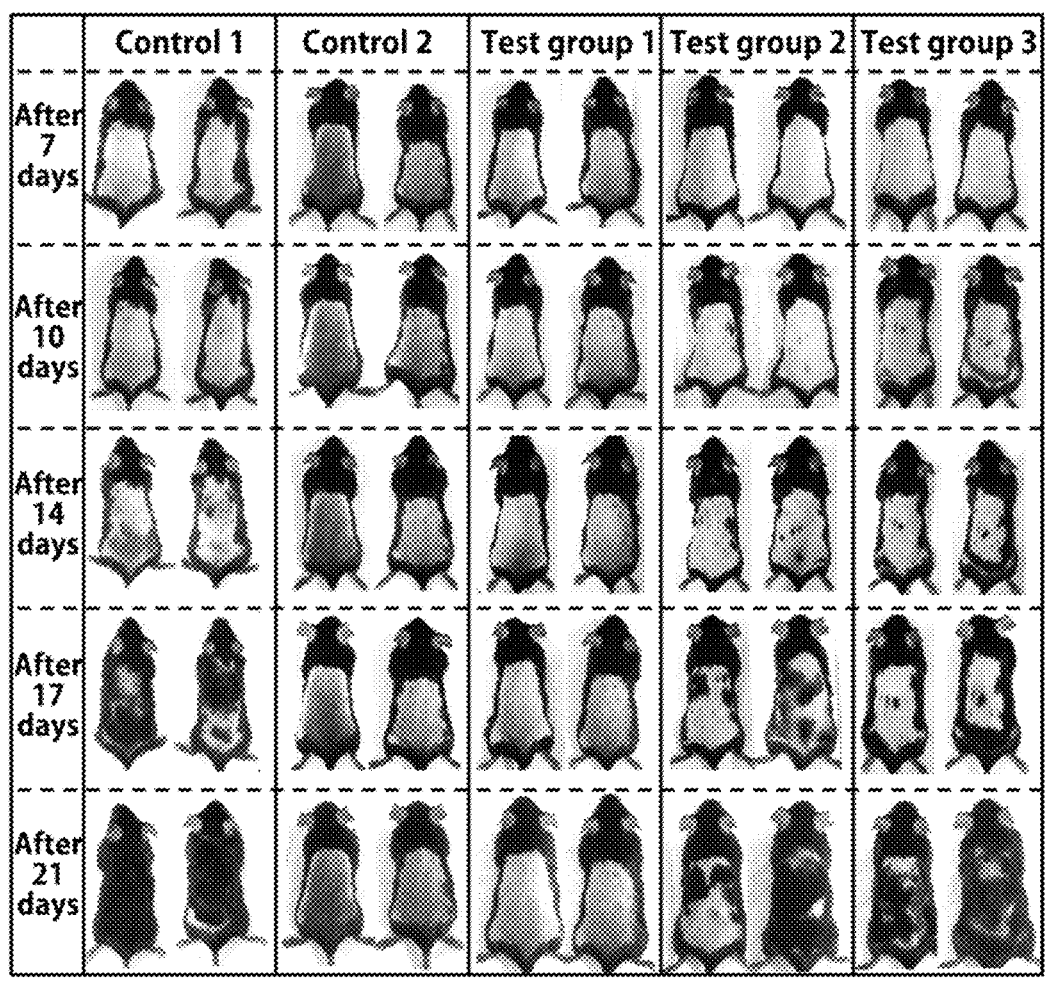
FIG. 15 shows images confirming whether a hair growth effect appears after repeated treatment of hair-loss-induced mice with the nanoliposome-microbubble conjugate of Example 2 according to the present invention once (test group 1), three times (test group 2) and five times (test group 3)

The above results are shown in FIG. 15. In control 2, hair was seldom grown after 21 days due to the effect of testosterone, whereas in test groups treated with the conjugate of Example 2 three times and five times (test groups 2 and 3), relatively large amounts of hair grew compared to control 2.

Test Example 6-3. SRD5A2 Expression in Mouse-Measurement of mRNA Expression Level The mouse was treated with the nanoliposome-microbubble conjugate (Cas9:gRNA (74 μg:26 μg)) of Example 2 according to the present invention, and after 24 hr, the mouse skin was obtained, and total RNA was extracted therefrom using TRIzol (Invitrogen) and cDNA was synthesized using SuprimeScript RT premix 2× (GeNetBio).

Real-time PCR for measuring mRNA expression of SRD5A2 was measured using SYBR green 2× Premix (Applied Biosystems) and an AB Step One Plus real-time PCR system (Applied Biosystems). As such, the base sequences of primers used for the detection were as follows.

SRD5A2 sense: GGCCTCTTCTGCGTAGATTA (SEQ ID NO: 44)

SRD5A2 antisense: CACCCAAGCTAAACCGTATG (SEQ ID NO: 45)

GAPDH sense: GCACCGTCAAGGCTGAGAA (SEQ ID NO: 46)

GAPDH antisense: AGGGATCTCGCTCCTGGAA (SEQ ID NO: 47)

Figure 16:
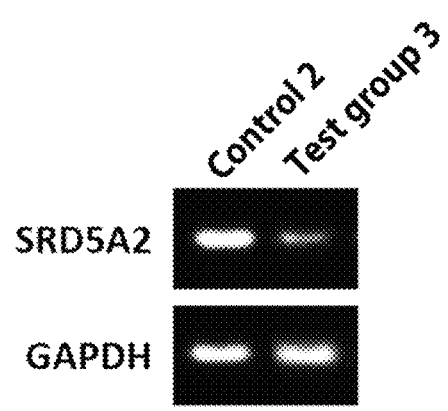
FIG. 16 shows the results of evaluation of the extent of SRD5A2 mRNA expression in mouse dermal tissue after treatment of a mouse with the nanoliposome-microbubble of Example 2 according to the present invention.

The above results are shown in FIG. 16, from which the mRNA expression of SRD5A2 can be concluded to be significantly reduced in dermal papilla cells due to treatment with the nanoliposome-microbubble conjugate of Example 2.

In conclusion, the nanoliposome-microbubble conjugate of the present invention is capable of fundamentally inhibiting the expression of SRD5A2 that induces hair loss, whereby the nanoliposome-microbubble conjugate is very effective at treating male hair loss.

The invention claimed is:

1. A nanoliposome-microbubble conjugate, in which a complex of a Cas9 protein, a guide RNA inhibiting SRD5A2 gene expression and a polyethyleneimine is encapsulated in a nanoliposome,
wherein the guide RNA inhibiting SRD5A2 gene expression comprises a base sequence of SEQ ID. NO: 1, 2, 3, 4 or 5.

2. The nanoliposome-microbubble conjugate of claim 1, wherein the nanoliposome includes lecithin, cholesterol, 1,2-dipalmitoyl-sn-glycero-3-phosphoethanolamine (DPPE) and DOGS-NTA-Ni lipid (1,2-dioleoyl-sn-glycero-3[(N-(5-amino-1-carboxypentyl)iminodiacetic acid)succinyl](nickel salt)).

3. The nanoliposome-microbubble conjugate of claim 1, wherein the nanoliposome is configured to bind to a monoclonal or polyclonal antibody able to recognize at least one protein selected from the group consisting of endoglin, CD34, keratin 18 and IL-6 (interleukin 6), which are expressed in dermal papilla cells.

4. The nanoliposome-microbubble conjugate of claim 1, wherein the microbubble includes 1,2-dipalmitoyl-sn-glyero-3-phosphocholine (DPPC), dicetyl phosphate (DCP), cholesterol, 1,2-dipalmitoyl-sn-glycero-3-phosphoethanolamine (DPPE) and 1,2-distearoyl-sn-glycero-3-phosphoethanolamine-N-poly(ethyleneglycol)-2000-N-[3-(2-pyridyldithio)propionate (DSPE-PEG-sPDP).

5. A composition for ameliorating or treating hair loss, containing the nanoliposome-microbubble conjugate of claim 1.

6. A method of preparing the nanoliposome-microbubble conjugate of claim 1, the method comprising:
forming a nanoliposome-microbubble conjugate by mixing a nanoliposome with a microbubble,
the nanoliposome being prepared by:
S1) preparing a complex of a Cas9 protein, a guide RNA inhibiting SRD5A2 gene expression and polyethyleneimine and preparing a lipid film composition by mixing lecithin, cholesterol, 1,2-dipalmitoyl-sn-glycero-3-phosphoethanolamine (DPPE) and DOGS-NTA-Ni lipid (1,2-dioleoyl-sn-glycero-3[(N-(5-amino-1-carboxypentyl)iminodiacetic acid)succinyl](nickel salt)) in chloroform;
S2) adding the lipid film composition with the complex of the Cas9 protein, the guide RNA inhibiting SRD5A2 gene expression and the polyethyleneimine and performing sonication;
S3) subjecting the sonicated lipid film composition to freezing-thawing and then sonication;
S4) centrifuging the lipid film composition sonicated in S3 and recovering a nanoliposome that is precipitated; and
S5) allowing an antibody to bind to the precipitated nanoliposome obtained in S4 using a crosslinking agent, and
the microbubble being prepared by:
A) preparing a lipid film composition by mixing 1,2-dipalmitoyl-sn-glyero-3-phosphocholine (DPPC), cholesterol, dicetyl phosphate (DCP), an amine-group-containing lipid and 1,2-distearoyl-sn-glycero-3-phosphoethanolamine-N-poly(ethyleneglycol)-2000-N-[3-(2-pyridyldithio)propionate (DSPE-PEG-sPDP) in chloroform;
B) adding a glucose solution to step A and performing sonication;
C) subjecting the lipid film composition sonicated in step B to freezing-thawing and then sonication; and
D) preparing a microbubble by introducing a hydrophobic gas into the lipid film composition sonicated in step C.

* * * * *